US008491557B2

(12) United States Patent
Kline et al.

(10) Patent No.: US 8,491,557 B2
(45) Date of Patent: *Jul. 23, 2013

(54) DISPOSABLE WEARABLE ABSORBENT ARTICLES WITH EXTENSIBLE SIDES

(75) Inventors: Mark James Kline, Okeana, OH (US); Henry William McCusker, III, Caracas (VE); Ronald Joseph Zink, II, Blue Ash, OH (US); Sarah Marie Young, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/279,625

(22) Filed: Oct. 24, 2011

(65) Prior Publication Data
US 2012/0041409 A1   Feb. 16, 2012

Related U.S. Application Data

(62) Division of application No. 11/971,973, filed on Jan. 10, 2008, now Pat. No. 8,062,278.

(60) Provisional application No. 60/879,682, filed on Jan. 10, 2007.

(51) Int. Cl.
*A61F 13/15* (2006.01)

(52) U.S. Cl.
USPC .............. 604/385.24; 604/385.25; 604/385.3; 604/386; 604/387; 604/389; 604/391; 604/396

(58) Field of Classification Search
USPC .................... 604/385.24, 385.25, 385.3, 386, 604/387, 389, 391, 394, 396
See application file for complete search history.

(56) References Cited

U.S. PATENT DOCUMENTS

| | | | |
|---|---|---|---|
| 5,143,679 A | 9/1992 | Weber et al. |
| 5,156,793 A | 10/1992 | Buell et al. |
| 5,167,897 A | 12/1992 | Weber et al. |
| 5,368,584 A | 11/1994 | Clear |
| 5,554,145 A | 9/1996 | Roe et al. |
| 5,705,013 A | 1/1998 | Nease |
| 5,899,895 A | 5/1999 | Robles |
| 5,906,008 A | 5/1999 | Heki et al. |
| 5,997,521 A | 12/1999 | Robles |
| 6,004,306 A | 12/1999 | Roe et al. |
| 7,028,735 B2 | 4/2006 | Schneider et al. |
| 7,056,411 B2 | 6/2006 | Desai et al. |

(Continued)

FOREIGN PATENT DOCUMENTS

| | | |
|---|---|---|
| EP | 1 319 380 A | 6/2003 |
| JP | 2006-102278 A | 4/2006 |
| WO | WO 2006/071434 A1 | 7/2006 |
| WO | WO 2007/069227 A | 6/2007 |

*Primary Examiner* — Jacqueline F. Stephens
(74) *Attorney, Agent, or Firm* — Thibault Fayette; Charles R. Ware

(57) ABSTRACT

Embodiments of the present disclosure include disposable wearable absorbent articles with extensible sides. In an embodiment of the present disclosure a disposable wearable absorbent article includes a front, a back, and an extensible side configured to connect the front and the back, wherein the extensible side has a substantially laterally extensible area, which includes a first area, bounded in part by at least a portion of a longitudinally outboard side edge. An overall lateral extensibility of the first area is substantially less than an overall lateral extensibility of the substantially laterally extensible area.

20 Claims, 27 Drawing Sheets

U.S. PATENT DOCUMENTS

| | | |
|---|---|---|
| 7,097,710 B2 | 8/2006 | Schneider |
| 7,169,228 B2 | 1/2007 | Schneider |
| 7,222,654 B2 | 5/2007 | Schneider et al. |
| 8,062,278 B2 * | 11/2011 | Kline et al. ............... 604/385.24 |
| 2004/0181200 A1 | 9/2004 | Desai et al. |
| 2004/0193133 A1 | 9/2004 | Desai et al. |
| 2005/0178494 A1 | 8/2005 | Schneider et al. |
| 2006/0004342 A1 | 1/2006 | Sawyer et al. |
| 2006/0069374 A1 | 3/2006 | Desai |
| 2006/0155256 A1 | 7/2006 | Desai |
| 2006/0271006 A1 | 11/2006 | Desai et al. |
| 2006/0271007 A1 | 11/2006 | Desai et al. |
| 2007/0142815 A1 | 6/2007 | Macura |
| 2008/0038507 A1 | 2/2008 | Seth |

* cited by examiner

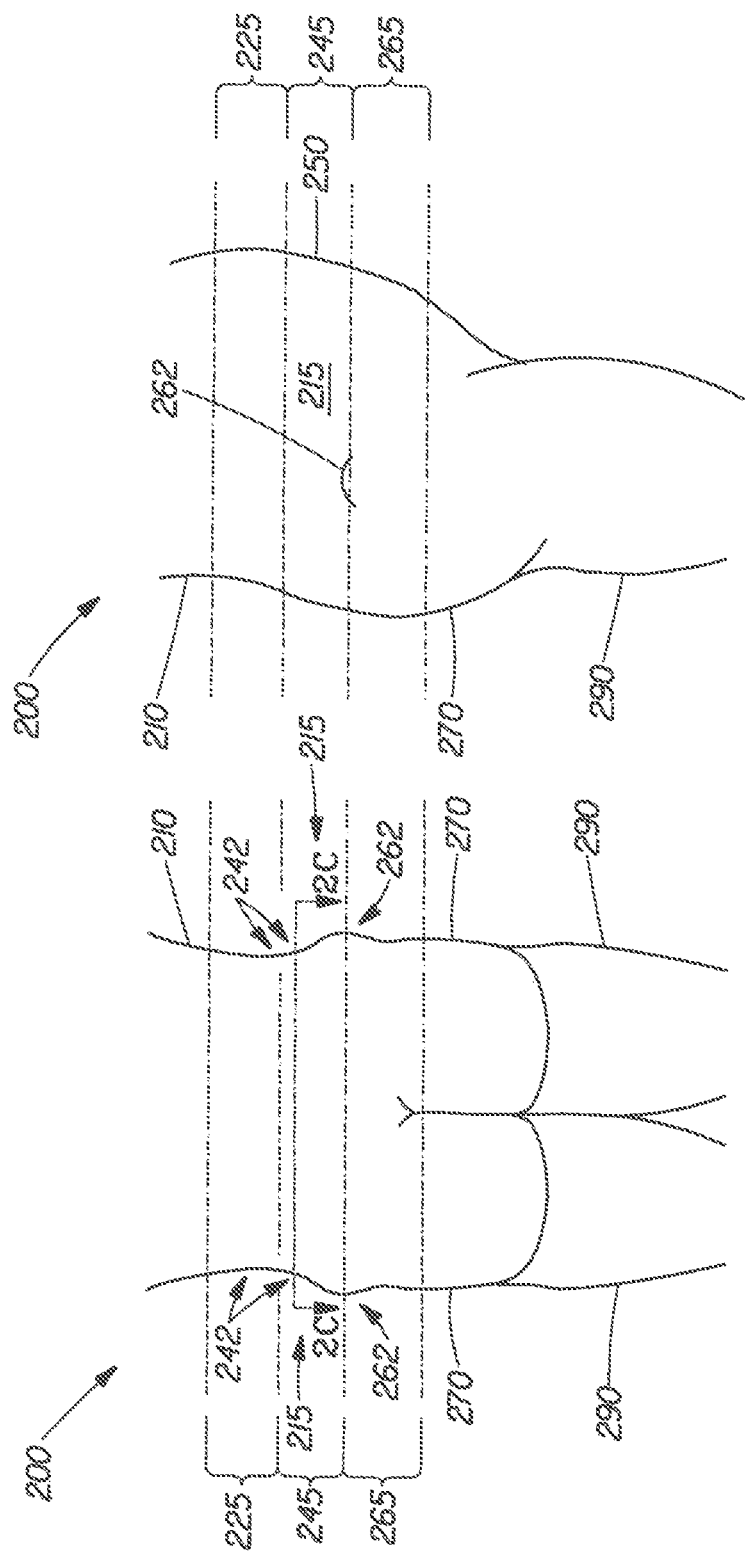

| | OVERALL LATERAL ELASTIC EXTENSIBILITIES | | | |
|---|---|---|---|---|
| EMBODIMENT | A1 | A2 | A3 | A4 |
| 1 | < <Aoll | | | |
| 2 | < <A2<br>< <A3<br>< <A4<br>< <Aoll | | | |
| 3 | < <A2<br>< <A3<br>< <A4<br>< <Aoll | =A3<br>=A4 | | |
| 4 | < <A2<br>< <A3<br>< <A4<br>< <Aoll | < <A3<br>< <A4 | | |
| 5 | < <A2<br>< <A3<br>< <A4<br>< <Aoll | < <A3 | | < <A3 |
| 6 | < <A2<br>< <A3<br>< <A4<br>< <Aoll | | | < <A2<br>< <A3 |
| 7 | < <A2<br>< <A3<br>< <A4<br>< <Aoll | | < <A2 | |
| 8 | < <A2<br>< <A3<br>< <A4<br>< <Aoll | | < <A4 | |

Fig. 7A

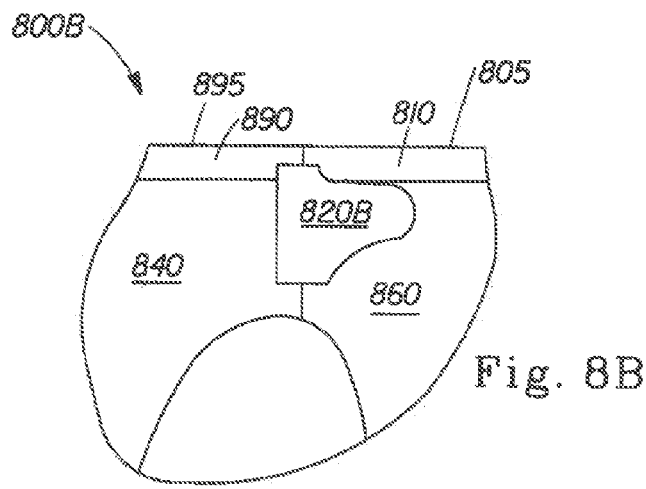
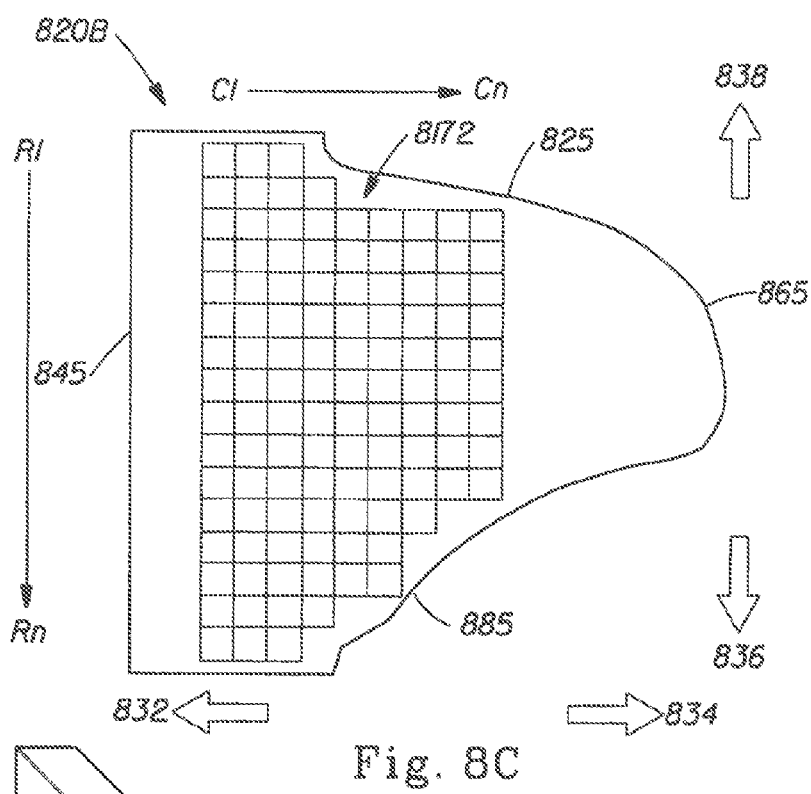
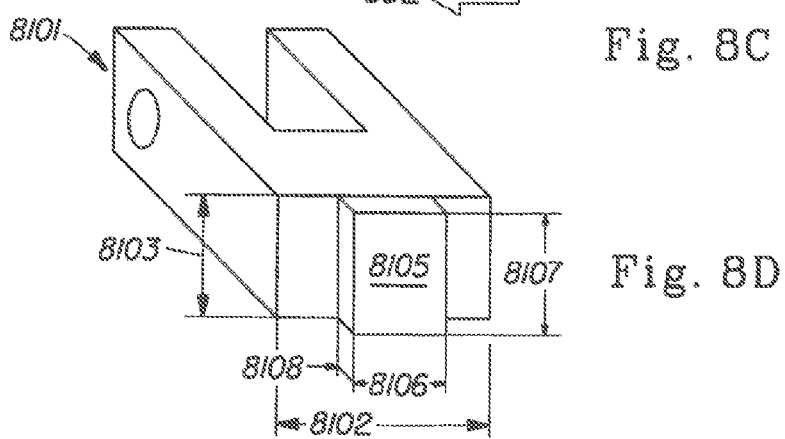

|  | C1 | C2 | C3 | C4 | C5 | C6 | C7 | C8 | C9 |
|---|---|---|---|---|---|---|---|---|---|
| R1 | 2.38 | 0.51 | 0.36 | | | | | | |
| R2 | 3.20 | 1.50 | 1.07 | 0.63 | | | | | |
| R3 | 3.43 | 1.97 | 1.22 | 0.86 | 0.79 | 0.76 | 0.84 | 0.93 | 2.28 |
| R4 | 3.67 | 2.36 | 1.16 | 0.94 | 0.79 | 0.67 | 0.83 | 1.11 | 2.34 |
| R5 | 3.90 | 1.85 | 0.83 | 0.83 | 0.74 | 0.70 | 0.85 | 1.13 | 2.60 |
| R6 | 3.67 | 0.96 | 0.77 | 0.73 | 0.74 | 0.74 | 0.96 | 1.11 | 2.76 |
| R7 | 3.49 | 0.87 | 0.70 | 0.74 | 0.74 | 0.74 | 0.96 | 1.12 | 2.74 |
| R8 | 3.39 | 0.85 | 0.64 | 0.74 | 0.77 | 0.76 | 0.96 | 1.31 | 2.82 |
| R9 | 3.50 | 0.74 | 0.71 | 0.79 | 0.76 | 0.76 | 0.86 | 1.07 | 2.38 |
| R10 | 3.45 | 0.85 | 0.66 | 0.75 | 0.74 | 0.67 | 0.87 | 1.17 | 2.44 |
| R11 | 3.91 | 0.82 | 0.70 | 0.78 | 0.78 | 0.78 | 0.99 | 1.15 | 2.04 |
| R12 | 3.95 | 0.86 | 0.75 | 0.80 | 0.77 | 0.71 | 0.86 | | |
| R13 | 3.67 | 0.78 | 0.69 | 0.77 | 0.79 | 0.76 | | | |
| R14 | 3.78 | 0.74 | 0.63 | 0.79 | 0.67 | 0.60 | | | |
| R15 | 3.81 | 0.69 | 0.60 | 0.68 | | | | | |
| R16 | 3.01 | 0.54 | 0.44 | | | | | | |

Fig. 8F

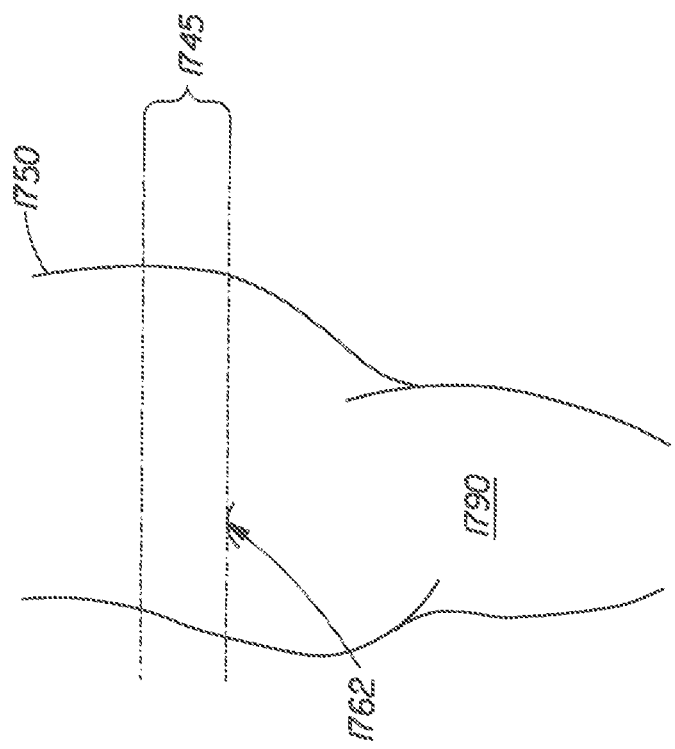
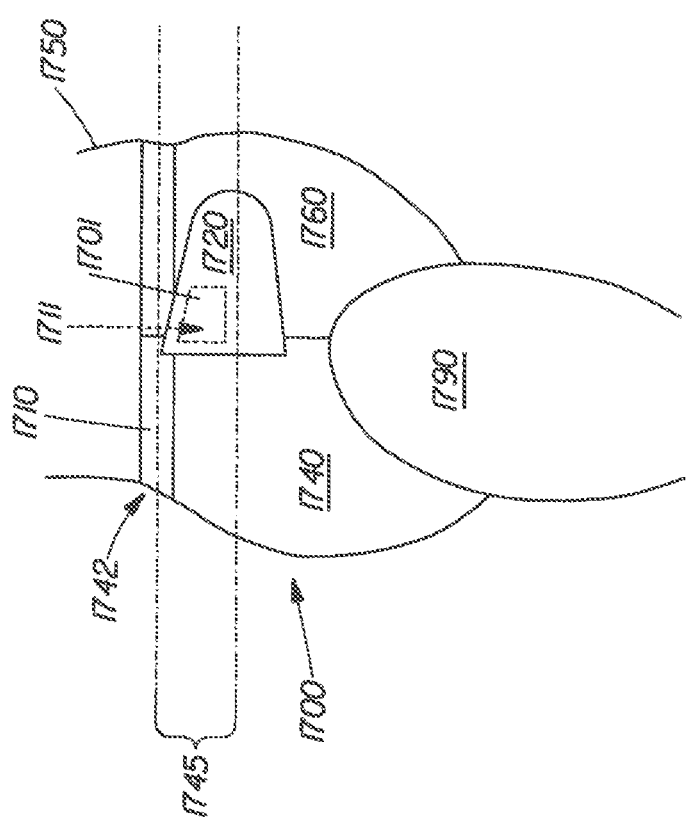
Fig. 17A
Fig. 17B

DISPOSABLE WEARABLE ABSORBENT ARTICLES WITH EXTENSIBLE SIDES

CROSS REFERENCE TO RELATED APPLICATIONS

This application is a divisional of U.S. application Ser. No. 11/971,973, filed on Jan. 10, 2008, now U.S. Pat. No. 8,062,278 which claims the benefit of U.S. Provisional Application No. 60/879,682, filed on Jan. 10, 2007, both of which are incorporated by reference herein.

FIELD

In general, embodiments of the present disclosure relate to disposable wearable absorbent articles. In particular, embodiments of the present disclosure relate to disposable wearable absorbent articles with extensible sides.

BACKGROUND

Disposable wearable absorbent articles include diapers and incontinence garments. These articles can be made from various materials, including extensible materials. Extensible materials can be extended in size. This ability to extend can be useful in disposable wearable articles. For example, a disposable wearable absorbent article with extensible sides can be extended to fit wearers of various sizes.

The design of such extensible sides can affect the way that an article can be applied to a wearer. Unfortunately, some disposable wearable absorbent articles with extensible sides are difficult to apply to wearers. For example, some disposable wearable absorbent articles can require significant forces to extend the extensible sides.

The design of such extensible sides can also affect the way that an article fits on a wearer. Unfortunately, some disposable wearable absorbent articles with extensible sides fit wearers poorly. For example, some disposable wearable absorbent articles with extensible sides can rotate around or slip down on a wearer. A disposable wearable absorbent article that rotates or slips can feel uncomfortable, look unattractive, and perform poorly as the article tends to ride back, sag, and leak.

BRIEF DESCRIPTION OF THE DRAWINGS

FIG. 2A illustrates a back view of a portion of a human body.

FIG. 2B illustrates a side view of the portion of the human body of FIG. 2A.

FIG. 7A is a chart illustrating various relationships of lateral extensibilities for areas of a substantially laterally extensible area of an extensible side of a disposable wearable absorbent article according to embodiments of the present disclosure.

FIG. 8B illustrates a perspective view of a disposable wearable absorbent article with extensible side ears, formed for wearing, according to embodiments of the present disclosure.

FIG. 8C illustrates an enlarged view of the extensible side ear of the disposable wearable absorbent article of the embodiment of FIG. 8B, unfastened and cut from the article and marked with a map for testing with a modulus mapping method, according to embodiments of the present disclosure.

FIG. 8D illustrates a modified pneumatic grip, for use in the modulus mapping method, according to embodiments of the present disclosure.

FIG. 8F illustrates an exemplary chart with directional modulus of elasticity values, obtained from the modulus mapping method testing and recorded for each square of the map of the embodiment of FIG. 8C, according to embodiments of the present disclosure.

FIG. 17A illustrates a side view of a disposable wearable absorbent article with extensible side ears as worn on a wearer according to embodiments of the present disclosure.

FIG. 17B illustrates a side view of the wearer of FIG. 17A.

DETAILED DESCRIPTION

Figure 1A:
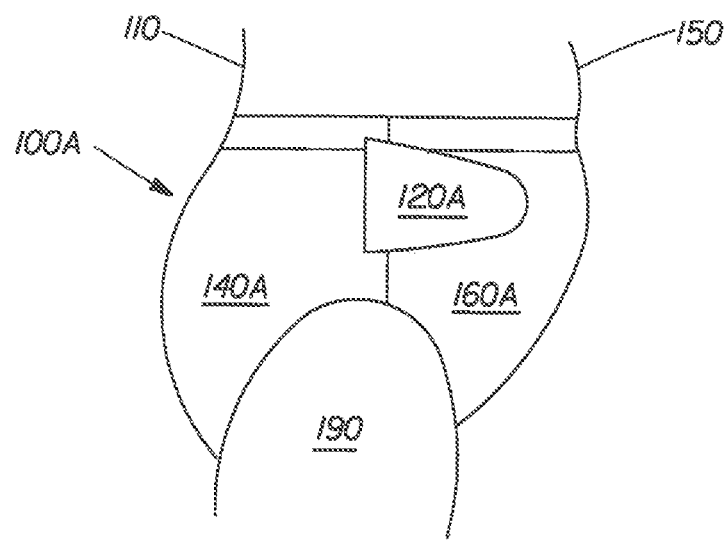
FIG. 1A illustrates a side view of a disposable wearable absorbent article with extensible side ears as worn on a wearer according to embodiments of the present disclosure.

Embodiments of the present disclosure include disposable wearable absorbent articles with extensible sides that are easy to apply and that fit wearers well. The designs of these articles allow the extensible sides to extend with reasonably low forces. The designs of these articles also help prevent the articles from rotating around or slipping down on a wearer. The disposable wearable absorbent articles of the present disclosure can feel comfortable, look attractive, and perform well as the articles tends to fit snugly, stay in place, and not leak.

Throughout the present disclosure, various figures illustrate human bodies. As a whole, these figures are intended to illustrate the presence of various external human anatomical features and general relationships between these features. For ease of reference, the present disclosure refers to many of these features using simple and informal terminology. These human anatomical features can relate to disposable wearable absorbent articles with extensible sides, according to embodiments of the present disclosure. Some figures are intended to illustrate how such disposable wearable articles can fit on human bodies of wearers.

In the present disclosure, figures that illustrate human bodies are not intended to illustrate all human anatomical features. These figures are also not intended to teach precise details or exact proportions of the human anatomical features that are illustrated. Further, these figures are not intended to limit embodiments of the present disclosure to any particular size, shape, or type of human body.

Throughout the present disclosure, the following terms have the following meanings, unless otherwise indicated. The terms "extensible" and "extensibility" refer to an ability of a material to extend in size from an original dimension to an extended dimension when subjected to a tensile force. The terms "elastically extensible" and "elastic extensibility" refer to an ability of an extensible material to extend in size from an original dimension to an extended dimension when subjected to a tensile force and to subsequently retract from the extended dimension to approximately the original dimension when relieved of the tensile force. The term "extensible without recovery" refers to characteristics of materials which upon application of a tensile force, can stretch to an elongated length of at least about 110%, preferably 125% of its relaxed, original length (i.e. can stretch to elongations of 10%, preferably 25% more than its original length), without rupture or breakage, and upon release of the force, shows little recovery; for example, the recovery can be less than about 40%, preferably less than about 20% and more preferably less than about 10% of the length to which the material was extended beyond its original length. The term "substantially," when used to describe a relative quantitative difference (e.g. substantially greater than or substantially less than), refers to a difference of at least 25%.

Embodiments of the present disclosure can be used in disposable wearable absorbent articles with various extensible sides, such as elastically extensible sides or sides that are extensible without recovery.

FIG. 1A illustrates a side view of a disposable wearable absorbent article 100A with extensible side ears 120A as worn on a wearer according to embodiments of the present disclosure. In some embodiments, a disposable wearable absorbent article, such as the disposable wearable absorbent article 100A, can also be referred to as a refastenable diaper. The disposable wearable absorbent article 100A includes the extensible side ears 120A, a back 140A, and a front 160A. The wearer includes a back 110, a belly 150, and upper legs 190.

The extensible side ears 120A are configured to connect the front 160A and the back 140A of the absorbent article 100A. In the embodiment of FIG. 1A, the extensible side ears 120A are durably connected to the back 140A and refastenably connected to the front 160A. Extensible side ears can be configured to connect a front and a back of a disposable wearable absorbent article in a number of ways, as will be understood by one of ordinary skill in the art. In various embodiments, the extensible side ears 120A can be extensible side ears 320 of the embodiment of FIG. 3 or an extensible side ear 520 of the embodiment of FIG. 5. Throughout the present disclosure, the term "extensible side" is intended to include extensible side ears, such as the extensible side ears 120A, unless otherwise indicated. The disposable wearable absorbent article 100A can, in some embodiments, be a disposable wearable absorbent article 300 of the embodiment of FIG. 3.

Figure 1B:
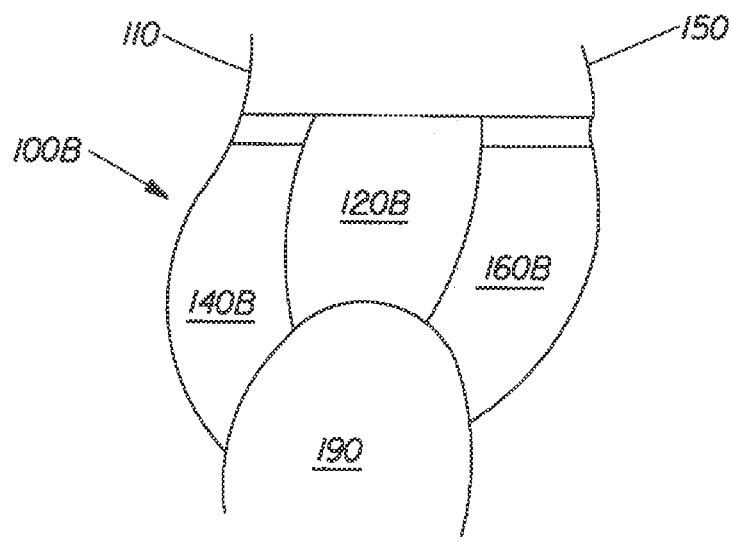
FIG. 1B illustrates a side view of a disposable wearable absorbent article with extensible side panels as worn on a wearer according to embodiments of the present disclosure.

FIG. 1B illustrates a side view of a disposable wearable absorbent article 100B with extensible side panels 120B as worn on a wearer according to embodiments of the present disclosure. In some embodiments, a disposable wearable absorbent article, such as the disposable wearable absorbent article 100B, can also be referred to as a pant diaper. The disposable wearable absorbent article 100B includes the extensible side panels 120B, a back 140B, and a front 160B. The wearer includes a back 110, a belly 150, and upper legs 190.

The extensible side panels 120B are configured to connect the front 160B and the back 140B of the absorbent article 100B. In the embodiment of FIG. 1B, each of the extensible side panels 120B is illustrated as a single piece of material however, in various embodiments of the present disclosure, an extensible side panel can be constructed from two or more pieces of material durably and/or refastenably connected together, as will be understood by one of ordinary skill in the art. In the embodiment of FIG. 1B, the extensible side panels 120B are durably connected to the back 140B and durably connected to the front 160B. Extensible side panels can be configured to durably and/or refastenably connect a front and/or a back of a disposable wearable absorbent article in a number of ways, as will be understood by one of ordinary skill in the art. In various embodiments, the extensible side panels 120B can be extensible side panels 420 of the embodiment of FIG. 4 or an extensible side panel 620 of the embodiment of FIG. 6. Throughout the present disclosure, the term "extensible side" is intended to include extensible side panels, such as the extensible side panels 120B, unless otherwise indicated. The disposable wearable absorbent article 100B can, in some embodiments, be a disposable wearable absorbent article 400 of the embodiment of FIG. 4.

Figure 2C:
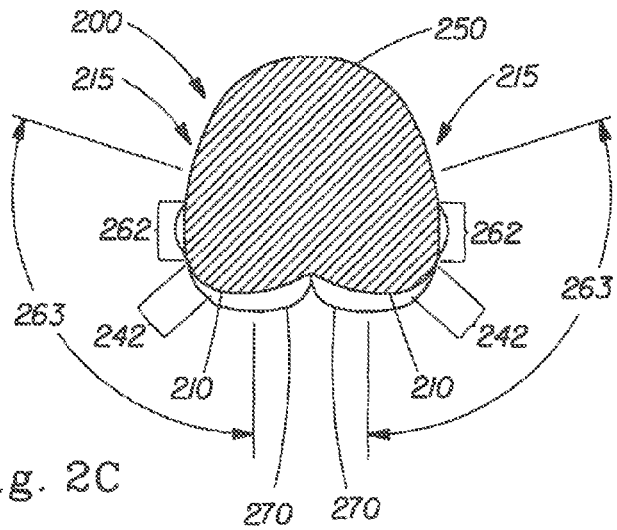
FIG. 2C illustrates a cross-sectional view of a portion of the human body of FIG. 2A.

FIG. 2A illustrates a back view of a portion of a human body 200, standing substantially upright on the ground. The human body 200 includes a back 210, sides 215, a lower back region 225, small radius portions 242, upper hips 245, posterior hip inflection protrusions (PHIPs) 262, lower hips 265, buttocks 270, and upper legs 290. The lower back region 225 is located in a lower region of the back 210, above the upper hips 245. The upper hips 245 are located immediately above the PHIPs 262. The lower hips 265 are located immediately below the PHIPs 262. In FIG. 2A, the locations of the lower back region 225, the upper hips 245, and the lower hips 265 are indicated by reference lines, which extend into FIG. 2B. In the upper hips 245, FIG. 2A also includes section lines C-C, used in connection with FIG. 2C, as described below. The features of the human body 200 illustrate how disposable wearable articles can fit on wearers.

The PHIP 262 is a protruding portion on a convex surface of the hips toward the back 210 of the human body 200. The PHIP 262 is a local ridge on that convex surface, formed by underlying tissue in the human body. In the back view of FIG. 2A, the PHIPs 262 are illustrated as ridges located between the upper hips 245 and the lower hips 265. For clarity, the PHIPs 262 of FIG. 2A are illustrated as pronounced features. However, on some human bodies, a PHIP can appear as a less pronounced ridge. A method of locating a PHIP is provided following the description of FIG. 2C.

Different pathways on the surface of a human body can have different pathlengths. Different pathlengths can affect how extensible materials can be extended over various pathways on a human body. A disposable wearable absorbent article can include extensible sides, which can be extended at least partway around a wearer when the article is worn. The extensible sides can be designed to help the article stay in place on the wearer.

Where an extensible side is extended along a pathway with a longer pathlength, the side extends in greater tension. Where the extensible side is extended along a pathway with a shorter pathlength, the side extends in lesser tension. A disposable wearable absorbent article can include an extensible side, in which a first portion of the side can be extended around a wearer along a pathway with a longer pathlength while a second portion of the extensible side can be extended around the wearer along a pathway with a shorter pathlength. Thus, the first portion can be extended in greater tension while the second portion can be extended in lesser tension. For example, a lower portion of an extensible side can be extended around a longer pathlength and into greater tension, while an upper portion of the extensible side can be extended around a shorter pathlength and into lesser tension.

In contrast with this example, where an upper portion of an extensible side of a disposable wearable absorbent article is extended into greater tension, tensile forces can be directed through the upper portion of the extensible side to an upper portion of the article proximate to a waist edge of the article, such as a waistband. In various embodiments of the present disclosure, a disposable wearable absorbent article with extensible sides can be designed to create greater tension in upper portions of the extensible sides allowing the extensible sides to extend easily and helping the article to fit snugly, stay in place, and not leak.

FIG. 2B illustrates a side view of the portion of the human body 200 of FIG. 2A. The human body 200 includes the back 210, the side 215, the lower back region 225, the upper hips 245, a belly 250, the PHIP 262, the lower hips 265, the buttocks 270, and the upper legs 290. The locations of the lower back region 225, the upper hips 245, and the lower hips 265 are indicated by reference lines, which extend from FIG. 2A.

FIG. 2C illustrates a cross-sectional view of a portion of the human body 200 of FIG. 2A, taken at a sectioning plane and in a direction indicated by the section lines C-C in FIG. 2A. The human body 200 includes the back 210, the sides 215, small radius portions 242, the belly 250, the PHIPs 262, a PHIP region 263, and the buttocks 270. The features of the human body 200 illustrate how disposable wearable articles can fit on wearers.

A PHIP can be found on a human body by using an imaging tool to find a local protrusion in a particular region of the human body. As illustrated in FIG. 2C, the PHIPs 262 are disposed in the PHIP regions 263. The left PHIP region 263 extends horizontally from about the middle of the left buttock 270 to about the middle of the left side 215. The right PHIP region 263 extends horizontally from about the middle of the right buttock 270 to about the middle of the right side 215. The PHIP regions extend vertically between about just above the anterior superior iliac crest and about the top of the legs. The cross-sectional portion illustrated in FIG. 2C is taken at the top of the PHIP region 263.

A PHIP can be found in a PHIP region by using a three-dimensional imaging tool, such as a 3dMD 5 pod torso photographic system (available from 3dMD in Atlanta, Ga.). The three-dimensional imaging tool can scan an outer surface of a human body, accurately measuring the topography of the surface and recording those measurements. Such an imaging tool can locate a vertical centerline in a PHIP region of a scanned human body and determine the distances from that centerline to points on the surface of the body. For an upright human body, the vertical centerline is considered to be perpendicular to the ground, substantially parallel to an imaginary line running from the body's head to the body's toes. For a human body lying parallel to the ground, scanned coordinates can be transformed, so that the centerline for that body that is substantially parallel to an imaginary line running from the body's head to the body's toes is also considered to be a "vertical" centerline.

Figure 2D:
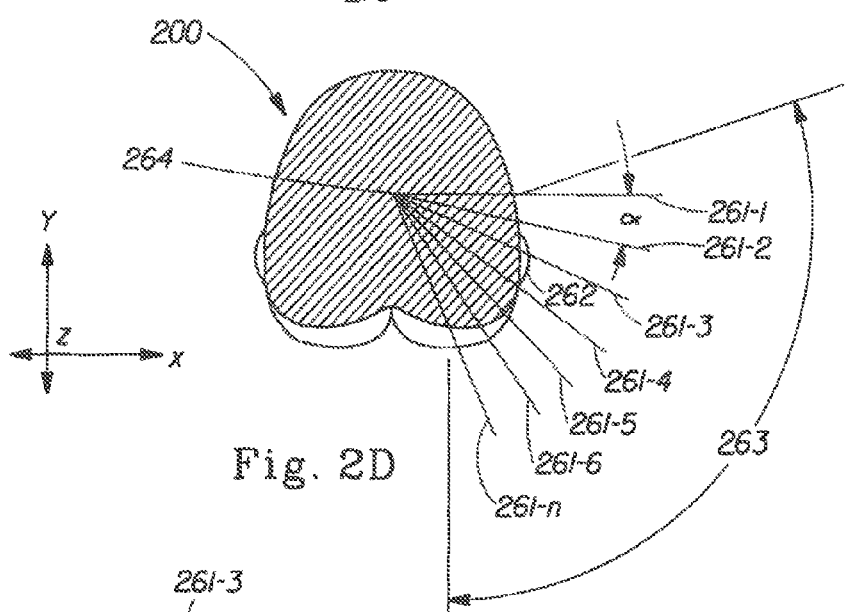
FIG. 2D illustrates an enlarged view of the cross-sectional view of the portion of the human body of FIG. 2C.

FIG. 2D illustrates an enlarged view of the cross-sectional view of the portion of the human body 200 of FIG. 2C, including the right PHIP region 263, a vertical centerline 264 for the cross-section, and sectioning planes 261-1 through 261-N. In FIG. 2D, a reference coordinate system indicates an x-y plane parallel to the ground on which the human body 200 is standing upright and a z direction perpendicular to the ground. The vertical centerline 264 can be determined by the three-dimensional imaging tool, as described above.

The three-dimensional imaging tool can also find dimensions on the surface of the human body 200 in each of the sectioning planes 261-1 through 261-N. In the embodiment of FIG. 2D, seven sectioning planes are shown, although other numbers of sectioning planes can be used. Each of the sectioning planes is oriented parallel to the z direction and passes through the vertical centerline 264. The sectioning planes are radially spaced apart at regular angular intervals, alpha, throughout the PHIP region 263, as illustrated in FIG. 2D. The angular intervals should be small enough so that the topographical changes on the surface of the human body 200 can be detected with an appropriate granularity, as will be understood by one of ordinary skill in the art. As an example, the angle alpha can be 5 degrees. As a result, the sectioning planes 261-1 through 261-N collectively sweep through the PHIP region 263 in series, accurately measuring the topography of the surface of the human body.

Figure 2E:
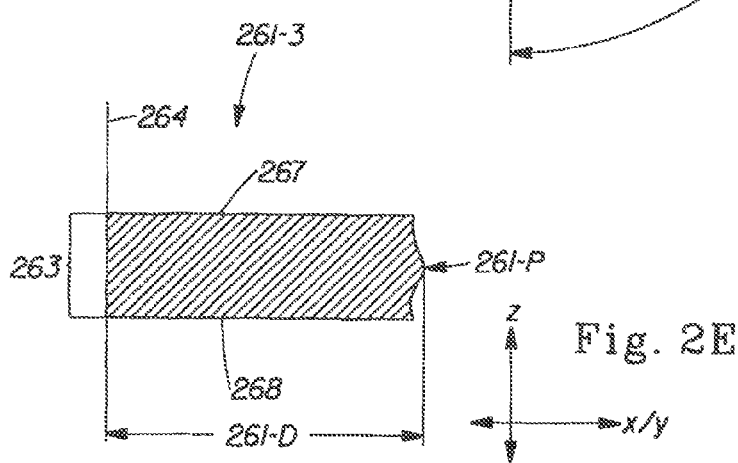
FIG. 2E illustrates a side view of a portion of the cross-sectional view of the portion of the human body of FIG. 2D, taken at a particular sectioning plane.

FIG. 2E illustrates a side view of a portion of the cross-section of the portion of the human body 200 of FIG. 2D, taken at sectioning plane 261-3. The sectioning plane 261-3 is in the PHIP region 263, coincides with the vertical centerline 264 (which is parallel to the z-direction) and extends from a top 267 of the PHIP region 263 to a bottom 268 of the PHIP region 263. A local peak in a region on a surface of a human body will have the largest distance from the vertical centerline, within the region. When the three-dimensional imaging tool locates the largest centerline distance in a region, it locates a local peak. In the portion of the human body 200 in the sectioning plane 261-3, the largest distance from the vertical centerline is 261-D, for the local peak 261-P. The local peak 261-P is a point on the PHIP 262. Since a PHIP is a local ridge-like protrusion, a PHIP can be found by examining the sectioning planes 261-1 through 261-N and finding a series of local peaks, in consecutive sectioning planes within the PHIP region 263, as will be understood by one of ordinary skill in the art. By using this method, a PHIP can be found on a human body.

Each small radius portion 242 is a portion of a surface of the human body 200, adjacent to the PHIP 262, where the side 215 of the human body 200 curves around to the back 210. A radius of curvature of each small radius portion 242 is typically smaller than curvatures of nearby body parts, such as the back 210. The small radius portions 242 can be convenient locations for fitting an upper portion of a disposable wearable article proximate to a waist edge.

A disposable wearable absorbent article can include an upper portion proximate to a waist edge, which can wrap at least partway around a wearer when the article is worn. Where an upper portion wraps around a smaller radius of curvature, the upper portion fits more snugly. This is due to the physics of a flexible material that is wrapped around a curved surface and placed under tension. In this scenario, as a tensile force places the flexible material under tension, the flexible material exerts a normal force perpendicular to and inward on the curved surface. According to the basic Capstan formula, the normal force is proportional to the tensile force divided by the radius of the curved surface. Thus, at a given tensile force as the radius becomes smaller the normal force becomes larger. Since each of the small radius portions 242 has a relatively smaller radius of curvature, an upper portion can fit more snugly on these portions of the human body 200. In various embodiments of the present disclosure, a disposable wearable absorbent article with extensible sides can be designed to direct tensile forces through the extensible sides to an upper portion which wraps around small radius portions of a wearer, allowing the extensible sides to extend easily and helping the article to fit snugly, stay in place, and not leak.

Figure 3:
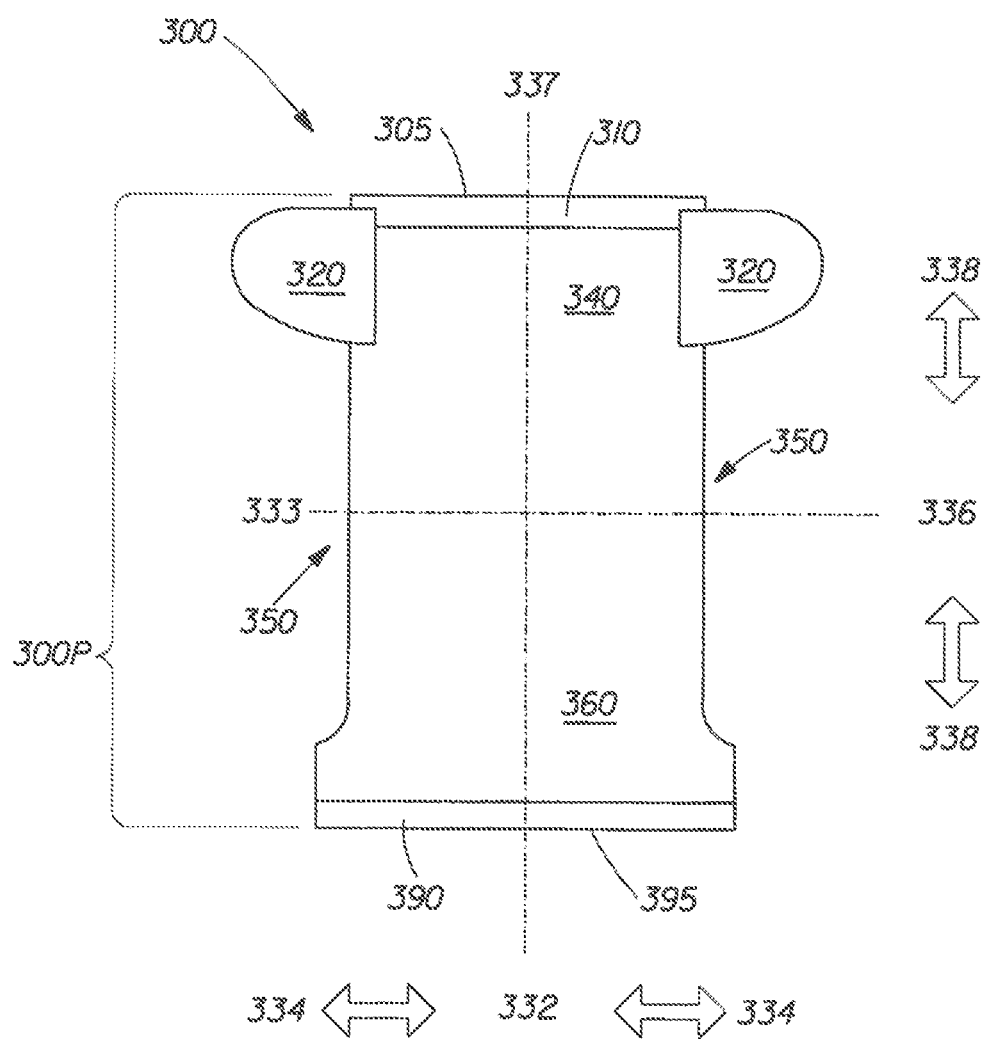
FIG. 3 illustrates a top view of an embodiment of a disposable wearable absorbent article with extensible side ears according to the present disclosure.

FIG. 3 illustrates a top view of an embodiment of a disposable wearable absorbent article 300 with extensible side ears 320 according to the present disclosure. FIG. 3 illustrates an outside of the disposable wearable absorbent article 300. The disposable wearable absorbent article 300 includes a back waist edge 305, a back upper portion 310, the extensible side ears 320, a back 340, a crotch area 350, a front 360, a front upper portion 390, and a front waist edge 395. The article 300 has an article pitch 300P, which is a longitudinal dimension measured from the back waist edge 305 to the front waist edge 395, when the article 300 is laid out flat. The extensible side ears 320 are configured to connect the front 360 and the back 340 of the absorbent article 300. In the embodiment of FIG. 3, the extensible side ears 320 are durably connected to the back 340 and refastenably connectable to the front 360. For clarity, FIG. 3 does not illustrate all details of the disposable wearable absorbent article 300. The disposable wearable absorbent article 300 can, in some embodiments, be the disposable wearable absorbent article 100A of the embodiment of FIG. 1A. Also, in various embodiments, either or both of the extensible side ears 320 can be a side ear 520 of the embodiment of FIG. 5.

In FIG. 3, a lateral centerline 333 and a longitudinal centerline 337 provide lines of reference for referring to relative locations of parts of the disposable wearable absorbent article 300. When a first part is nearer to the longitudinal centerline 337 than a second part, the first part can be considered laterally inboard to the second part. Similarly, the second part can be considered laterally outboard from the first part. When a third part is nearer to the lateral centerline 333 than a fourth part, the third part can be considered longitudinally inboard to the fourth part. Similarly, the fourth part can be considered longitudinally outboard from the third part. FIG. 3 includes arrows indicating relative directions for laterally inboard 332, laterally outboard 334, longitudinally inboard 336, and longitudinally outboard 338, with respect to the disposable wearable absorbent article 300. Throughout the present disclosure, unless otherwise stated, a reference to a lateral dimension, measurement, line, or direction refers to a dimension, measurement, line, or direction parallel to the lateral centerline 333 and a reference to a longitudinal dimension, measurement, line, or direction refers to a dimension, measurement, line, or direction parallel to the longitudinal centerline 337.

Figure 4:
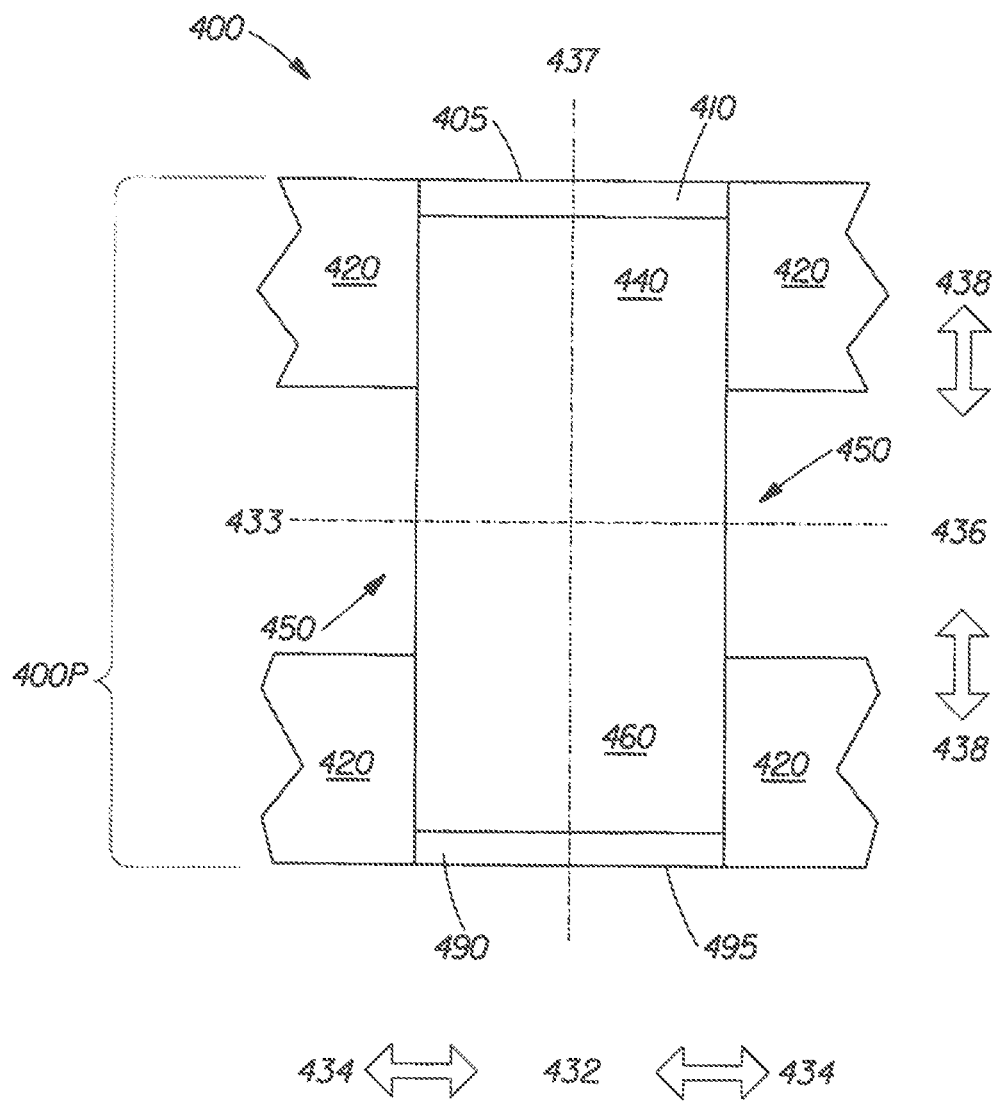
FIG. 4 illustrates a top view of an embodiment of a disposable wearable absorbent article with extensible side panels according to the present disclosure.

FIG. 4 illustrates a top view of an embodiment of a disposable wearable absorbent article 400 with extensible side panels 420 according to the present disclosure. FIG. 4 illustrates an outside of the disposable wearable absorbent article 400. The disposable wearable absorbent article 400 includes a back waist edge 405, a back upper portion 410, the extensible side panels 420, a back 440, a crotch area 450, a front 460, a front upper portion 490, and a front waist edge 495. The article 400 has an article pitch 400P, which is a longitudinal dimension measured from the back waist edge 405 to the front waist edge 495, when the article 400 is laid out flat. In FIG. 4, a lateral centerline 433 and a longitudinal centerline 437 provide lines of reference for referring to relative inboard and outboard locations of parts of the disposable wearable absorbent article 400. FIG. 4 also includes arrows indicating relative directions for laterally inboard 432, laterally outboard 434, longitudinally inboard 436, and longitudinally outboard 438, with respect to the disposable wearable absorbent article 400.

The extensible side panels 420 are configured to connect the front 460 and the back 440 of the absorbent article 400. In the embodiment of FIG. 4, the extensible side panels 420 are durably connected to the back 440 and durably connected to the front 460. Laterally outboard edges of the extensible side panels 420 are illustrated as broken, since the extensible side panels 420 are separated when the disposable wearable absorbent article 400 is laid out flat, as illustrated in FIG. 4. For clarity, FIG. 4 does not illustrate all details of the disposable wearable absorbent article 400. The disposable wearable absorbent article 400 can, in some embodiments, be the disposable wearable absorbent article 100B of the embodiment of FIG. 1B. Also, in various embodiments, either or both of the extensible side panels 420 can be a side panel 620 of the embodiment of FIG. 6.

Figure 5:
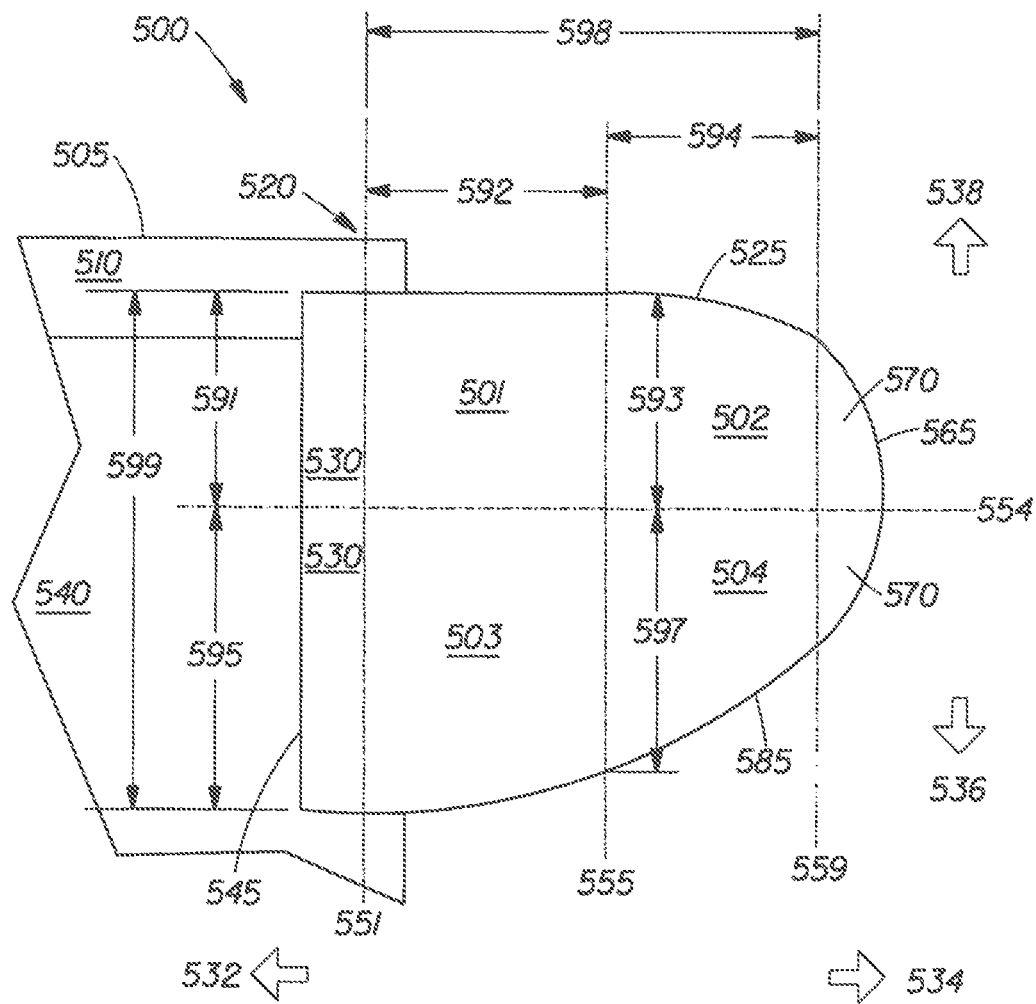
FIG. 5 illustrates a top view of an embodiment of an extensible side ear of a disposable wearable absorbent article according to the present disclosure.

FIG. 5 illustrates a top view of an embodiment of an extensible side ear 520 of a disposable wearable absorbent article 500 according to the present disclosure. In FIG. 5, the disposable wearable absorbent article 500 is illustrated in part. The extensible side ear 520 is durably connected to a back 540 of the disposable wearable absorbent article 500. FIG. 5 also illustrates a back waist edge 505 and a back upper portion 510 of the disposable wearable absorbent article 500. The extensible side ear 520 includes a first area 501, a second area 502, a third area 503, a fourth area 504, a laterally inboard margin 530, and a laterally outboard margin 570. The extensible side ear 520 also includes a longitudinally outboard side edge 525, a laterally inboard side edge 545, a laterally outboard side edge 565, and a longitudinally inboard side edge 585. The embodiment of FIG. 5 includes a first lateral reference line 551, a longitudinal reference line 554, a second lateral reference line 555, and a third lateral reference line 559. The embodiment of FIG. 5 also illustrates a first area longitudinal length 591, a second area longitudinal length 593, a third area longitudinal length 595, a fourth area longitudinal length 597, an overall area longitudinal length 599, a first lateral width 592, a second lateral width 594, and an overall area lateral width 598. FIG. 5 further includes arrows indicating relative directions for laterally inboard 532, laterally outboard 534, longitudinally inboard 536, and longitudinally outboard 538, with respect to the disposable wearable absorbent article 500.

The extensible side ear 520 includes a substantially laterally extensible area, which is substantially extensible in the lateral direction. In some embodiments, the substantially laterally extensible area can also be at least partially longitudinally extensible. The substantially laterally extensible area includes the first area 501, the second area 502, the third area 503, and the fourth area 504. The first lateral reference line 551, the second lateral reference line 555, and the third lateral reference line 559, divide the substantially laterally extensible area into laterally adjacent parts. The longitudinal reference line 554 divides the substantially laterally extensible area into longitudinally adjacent parts. In the embodiment of FIG. 5, the substantially laterally extensible area is bounded by the longitudinally outboard side edge 525, the first lateral reference line 551, the third lateral reference line 559, and the longitudinally inboard side edge 585. The substantially laterally extensible area has an overall width that is the overall area lateral width 598, which can be measured laterally from an intersection between the first lateral reference line 551 and the longitudinally outboard side edge 525 to an intersection between the third lateral reference line 559 and the longitudinally outboard side edge 525. The substantially laterally extensible area also has an overall length that is the overall area longitudinal length 599, which can be measured longitudinally from an intersection between the first lateral reference line 551 and the longitudinally outboard side edge 525 to an intersection between the first lateral reference line 551 and the longitudinally inboard side edge 585.

The first lateral reference line 551 is offset from the laterally inboard side edge 545 by the laterally inboard margin 530, however, in some embodiments, the laterally inboard margin 530 can be eliminated so that the first lateral reference line 551 coincides with the laterally inboard side 545, which in turn can form a laterally inboard boundary for the substantially laterally extensible area. Similarly, the third lateral reference line 559 is offset from the laterally outboard side edge 565 by the laterally outboard margin 570, however, in some embodiments, the outboard margin 570 can be eliminated so that the third lateral reference line 559 coincides with the laterally outboard side edge 565, which in turn can form a laterally outboard boundary for the substantially laterally extensible area.

In the embodiment of FIG. 5, the first area 501 is bounded by portions of the longitudinally outboard side edge 525, the first lateral reference line 551, the longitudinal reference line 554, and the second lateral reference line 555. The portion of the first lateral reference line 551 forms a laterally inboard portion of the boundary of the first area 501. That portion has a first area longitudinal length 591 measured longitudinally from an intersection between the first lateral reference line 551 and the longitudinally outboard side edge 525 to an intersection between the first lateral reference line 551 and the longitudinal reference line 554. The first area 501 has a first lateral width 592 measured laterally from an intersection between the first lateral reference line 551 and the longitudinally outboard side edge 525 to an intersection between the second lateral reference line 555 and the longitudinally outboard side edge 525. The first area 501 is disposed within a laterally inboard and longitudinally outboard portion of the substantially laterally extensible area.

In the embodiment of FIG. 5, the second area 502 is adjacent to and substantially laterally outboard from the first area 501, and bounded by portions of the longitudinally outboard side edge 525, the longitudinal reference line 554, the second lateral reference line 555, and the third lateral reference line 559. The portion of the second lateral reference line 555 forms a laterally inboard portion of the boundary of the second area 502. That portion has a second area longitudinal length 593 measured longitudinally from an intersection between the second lateral reference line 555 and the longitudinally outboard side edge 525 to an intersection between the second lateral reference line 555 and the longitudinal reference line 554. The second area 502 has a second lateral width 594 measured laterally from an intersection between the second lateral reference line 555 and the longitudinally outboard side edge 525 to an intersection between the third lateral reference line 559 and the longitudinally outboard side edge 525.

In the embodiment of FIG. 5, the third area 503 is adjacent to and substantially longitudinally inboard to the first area 501, and bounded by portions of the first lateral reference line 551, the longitudinal reference line 554, the second lateral reference line 555, and the longitudinally inboard side edge 585. The portion of the first lateral reference line 551 forms a laterally inboard portion of the boundary of the third area 503. That portion has a third area longitudinal length 595 measured longitudinally from an intersection between the first lateral reference line 551 and the longitudinal reference line 554 to an intersection between the first lateral reference line 551 and the longitudinally inboard side edge 585. The third area 503 has a first lateral width 592 measured laterally from an intersection between the first lateral reference line 551 and the longitudinally outboard side edge 525 to an intersection between the second lateral reference line 555 and the longitudinally outboard side edge 525.

In the embodiment of FIG. 5, the fourth area 504 is adjacent to and substantially laterally outboard from the third area 503, adjacent to and substantially longitudinally inboard to the second area 502, and bounded by portions of the longitudinal reference line 554, the second lateral reference line 555, the third lateral reference line 559, and the longitudinally inboard side edge 585. The portion of the second lateral reference line 555 forms a laterally inboard portion of the boundary of the fourth area 502. That portion has a fourth area longitudinal length 597 measured longitudinally from an intersection between the second lateral reference line 555 and the longitudinal reference line 554 to an intersection between the second lateral reference line 555 and the longitudinally inboard side edge 585. The fourth area 504 has a second lateral width 594 measured laterally from an intersection between the second lateral reference line 555 and the longitudinally outboard side edge 525 to an intersection between the third lateral reference line 559 and the longitudinally outboard side edge 525.

Each of the areas 501, 502, 503, and 504 can relate to one or more of the other areas in various relationships of lateral extensibilities or force ratios as described in connection with the embodiments of FIGS. 7A-7C. The areas 501, 502, 503, and 504 can, in some embodiments, respectively be the areas 801, 802, 803, and 804, of the embodiment of FIG. 8A.

The second lateral reference line 555 is located approximately midway between the first lateral reference line 551 and the third lateral reference line 559, so that the first lateral width 592 and the second lateral width 594 are each approximately half of the overall area lateral width 598. Also, the longitudinal reference line 554 is located approximately midway between the longitudinally outboard side edge 525 and the longitudinally inboard side edge 585, so that the first area longitudinal length 591 and the third area longitudinal length 595 are each approximately half of the overall area longitudinal length 599.

In some embodiments, a substantially laterally extensible area can vary in shape from the embodiment of FIG. 5. For example, a substantially laterally extensible area can have a laterally inboard boundary with one or more straight lines, wavy lines, irregularly shaped lines, angles, curves, and/or combinations of these. Where the laterally inboard boundary is not a single straight line, the first lateral reference line 551 can still be considered as a straight line parallel to the lateral centerline, and coincident with a furthest laterally inboard point on the laterally inboard boundary of the substantially laterally extensible area. Also as an example, a substantially laterally extensible area can have a laterally outboard boundary with one or more straight lines, wavy lines, irregularly shaped lines, angles, curves, and/or combinations of these. Where the laterally outboard boundary is not a single straight line, the third lateral reference line 559 can still be considered as a straight line parallel to the lateral centerline, and coincident with a furthest laterally outboard point on the laterally outboard boundary of the substantially laterally extensible area.

In various embodiments, a substantially laterally extensible area in a side ear can be an extension of a back of a disposable wearable absorbent article. In these embodiments, the laterally inboard side edge 545 can be considered as a straight line parallel to the lateral centerline, and coincident with a furthest laterally inboard point in a crotch area of the disposable wearable absorbent article 500. Part or all of the back of the disposable wearable absorbent article can be laterally extensible and/or laterally inextensible. In some embodiments, in which the back and the side are similarly substantially laterally extensible, the first lateral reference line 551 can coincide with the laterally inboard side 545, as described above.

In some embodiments, the laterally inboard margin 530 and/or the laterally outboard margin 570 can be substantially less laterally extensible than the substantially laterally extensible area. This difference in lateral extensibility can be measured as a difference in force to laterally extend. For example, a laterally inboard margin and/or a laterally outboard margin can require at least twenty percent more force per length than the substantially laterally extensible area to laterally extend to a particular laterally extended dimension, as described in connection with the embodiments of FIGS. 7B and 7C. Where the laterally inboard margin 530 and/or the laterally outboard margin 570 is substantially less laterally extensible than the substantially laterally extensible area, the first lateral reference line 551 does not coincide with the laterally inboard side edge 545, but rather is located based on the boundary between the differing margin and the substantially laterally extensible area.

In some embodiments, some or all of the side edges 525, 545, 565, and 585 can vary from the embodiment of FIG. 5, in size, shape, alignment, and orientation. These side edges can vary in size to accommodate side ears of various shapes and sizes. These side edges can also take various shapes, such as one or more straight lines, wavy lines, irregularly shaped lines, angles, curves, and/or combinations of these. Such variations in side edges can affect the size and/or shape of one or more of the areas 501, 502, 503, and 504, and/or the margins 530 and 570, in the extensible side ear 520.

The substantially laterally extensible area can be constructed from a number of different materials. For instance, the substantially laterally extensible area may comprise conventional elastic materials or stretch laminates. The stretch laminates may comprise a laminated structure known as live stretch. Live stretch includes stretching elastic and bonding the stretched elastic to a substrate. After bonding the stretched elastic is released causing it to contract, resulting in a "corrugated" substrate. The corrugated substrate can stretch as the corrugated portion is pulled to about the point that the substrate reaches at least one original flat dimension. The elastic is preferably stretched at least 25% and more preferably at least 100% of its relaxed length when it is bonded to the substrate.

Alternatively, the stretch laminate may comprise a mechanically activated stretch laminate such as a zero strain stretch laminate. Zero strain stretch laminates comprise a laminated structure which includes at least one substrate and at least one elastic element. The substrate is typically a non-elastic nonwoven and is attached to the elastic element in a face to face orientation such that the elastic element is joined to the substrate. The laminated structure is mechanically activated enabling it to stretch. Mechanical activation refers to a process wherein the nonwoven fibers of the non-elastic substrates are broken, and/or stretched, within the nonwoven so that the nonwoven is stretched in a direction along its surfaces and can be easily expanded in that direction by partial straightening of the fibers in the nonwoven. Zero-strain elastomeric laminates are described in U.S. Pat. No. 5,143,679 issued to Weber et al., U.S. Pat. No. 5,156,793 issued to Buell et al., and U.S. Pat. No. 5,167,897 issued to Weber.

The substantially laterally extensible area can include elastic strands or elastic films. Any suitable elastic film known in the art can be used. Suitable elastic films may comprise polypropylene, polyethylene, polyolefins, styrene-isoprene-styrene, styrene-butadiene-styrene, or combinations thereof. The basis weight of the films can range from about 10 gsm to about 100 gsm.

Suitable elastic strands can be made of a resilient elastic thermoplastic material. The elastic strands may be made from liquid elastic that is extruded through a die to achieve the desired strand elastic diameter and/or shape. The shape of the extruded elastic strands is not limited. For example, typical elastic strands have a circular cross sectional shape, but sometimes the elastic strands may have different shapes, such as a trilobal shape, or a flat (i.e., "ribbon" like) shape. Suitable elastic strand shapes include rectangles, circles, ellipses, diamonds, triangles, parallelograms, trapezoids, wedges or other sections of circles or ellipses, other polygons, or other irregular enclosed shapes. Furthermore, the thickness or diameter of the elastic strands may vary in order to accommodate a particular application. Typically, the thickness of elastic strands may be in the range of about 0.02 mm to about 1 mm and the basis weight is in the range of about 20 g/m$^2$ to about 300 g/m$^2$.

The elastic strands or films can be adhesively attached to the substrate, extruded onto the substrate, or printed onto the substrate. Suitable apparatuses for applying elastic strands in a longitudinal direction are described in U.S. Pat. No. 7,028,735 issued to Schneider, et al., and in U.S. Pat. No. 7,222,654 issued to Schneider, et al. Apparatuses for applying elastic strands in a transverse direction, an angle from the longitudinal direction, or in a curvilinear fashion are described in U.S. Publication No. US 2005-0178494 A1 entitled "Method of Placing Material Transversely on a Moving Web" filed on Feb. 13, 2004. Apparatuses for applying elastic strands in the longitudinal direction, an angle from the longitudinal direction, or in a curvilinear fashion are described in U.S. Pat. No. 7,169,228 issued to Schneider, et al, and in U.S. Pat. No. 7,097,710 issued to Schneider, et al.

Suitable apparatuses and methods for printing elastic elements in any orientation are described in U.S. Publication No. 2004-0181220A1 entitled "Variable Stretch Composites and Methods of Making the Composite" filed on Mar. 29, 2004, and in U.S. Publication No. 2004-0193133A1 entitled "Variable Stretch Composites and Methods of Making the Composite" filed on Mar. 29, 2004. For the printing of elastic strands, the individual elastic strands may be configured as lines or strands generally having widths less than about 2 mm and typically less than about 1 mm. Linear elastic strands may be configured as bands generally having widths between about 2 mm and about 20 mm and aspect ratios ranging from about 2:1 to about 100:1. Typically, the thickness of an elastic strand may be in the range of about 0.02 mm to about 5 mm and the basis weight is in the range of about 20 g/m$^2$ to about 300 g/m$^2$.

In various embodiments, one or more layers of some or all of the substantially laterally extensible area can be partially and/or completely mechanically activated using various activation processes, such as a SELF activation process as described in U.S. Pat. No. 5,518,801 issued to Chappel, et al. and in U.S. Pat. No. 5,554,145 issued to Roe, et al. The SELF activation process can be applied in various patterns including patterns with one or more bands of various widths and various lengths, which have not been activated by the SELF activation process.

Figure 6:
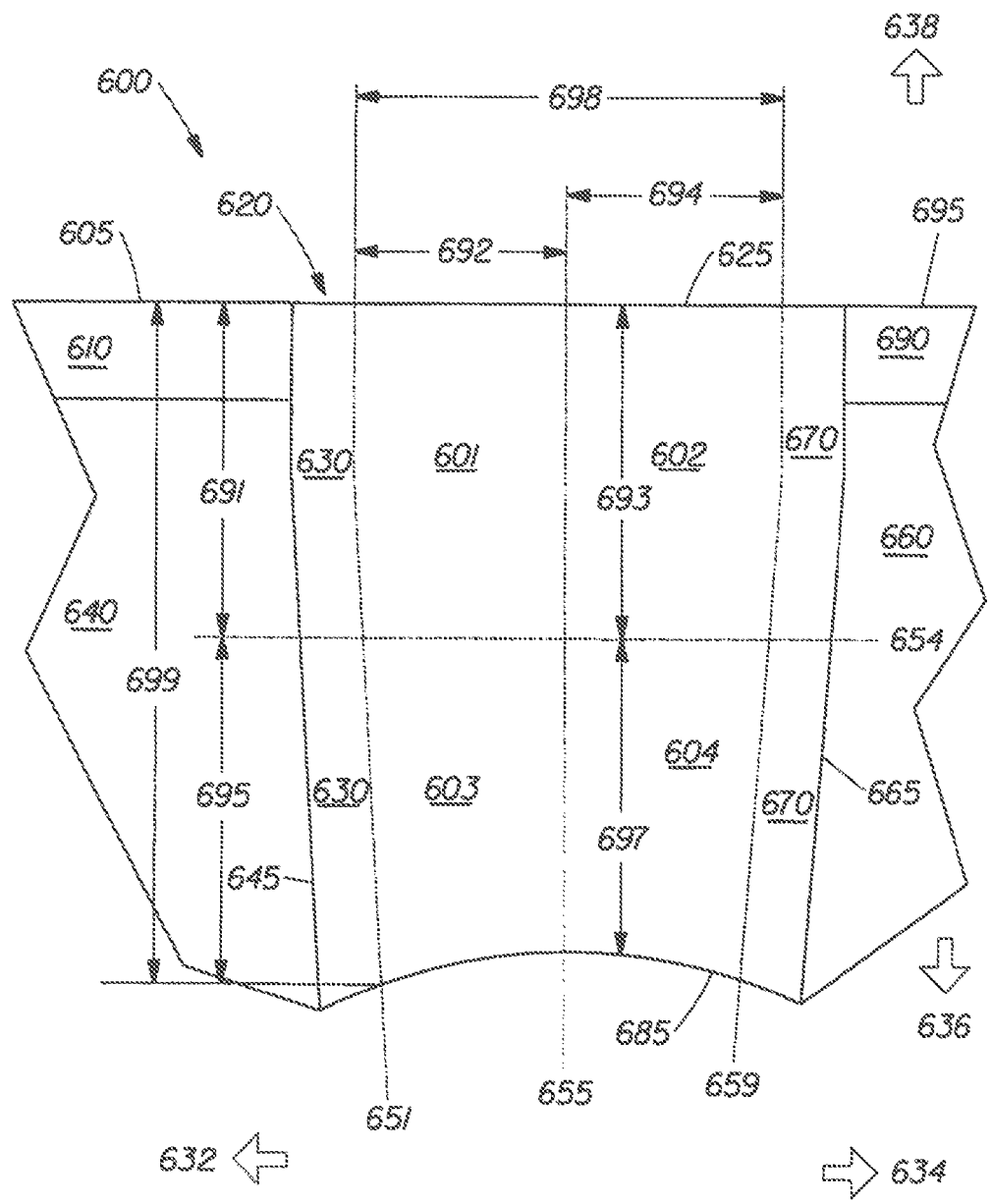
FIG. 6 illustrates a top view of an embodiment of an extensible side panel of a disposable wearable absorbent article according to the present disclosure.

FIG. 6 illustrates a top view of an embodiment of an extensible side panel 620 of a disposable wearable absorbent article 600 according to the present disclosure. In FIG. 6, the disposable wearable absorbent article 600 is illustrated in part. The extensible side panel 620 is durably connected to a back 640 and durably connected to a front 660 of the disposable wearable absorbent article 600. FIG. 6 also illustrates a back waist edge 605, a back upper portion 610, a front upper portion 690, and a front waist edge 695 of the disposable wearable absorbent article 600. The extensible side panel 620 includes a first area 601, a second area 602, a third area 603, a fourth area 604, a laterally inboard margin 630, and a laterally outboard margin 670. The extensible side panel 620 also includes a longitudinally outboard side edge 625, a laterally inboard side edge 645, a laterally outboard side edge 665, and a longitudinally inboard side edge 685. The embodiment of FIG. 6 includes a first lateral reference line 651, a longitudinal reference line 654, a second lateral reference line 655, and a third lateral reference line 659. The embodiment of FIG. 6 also illustrates a first area longitudinal length 691, a second area longitudinal length 693, a third area longitudinal length 695, a fourth area longitudinal length 697, an overall area longitudinal length 699, a first lateral width 692, a second lateral width 694, and an overall area lateral width 698. In various embodiments, one or more of the elements of the side panel 620 embodiment of FIG. 6 can be the like-numbered element of the side ear 520 embodiment of FIG. 5.

Figure 8A:
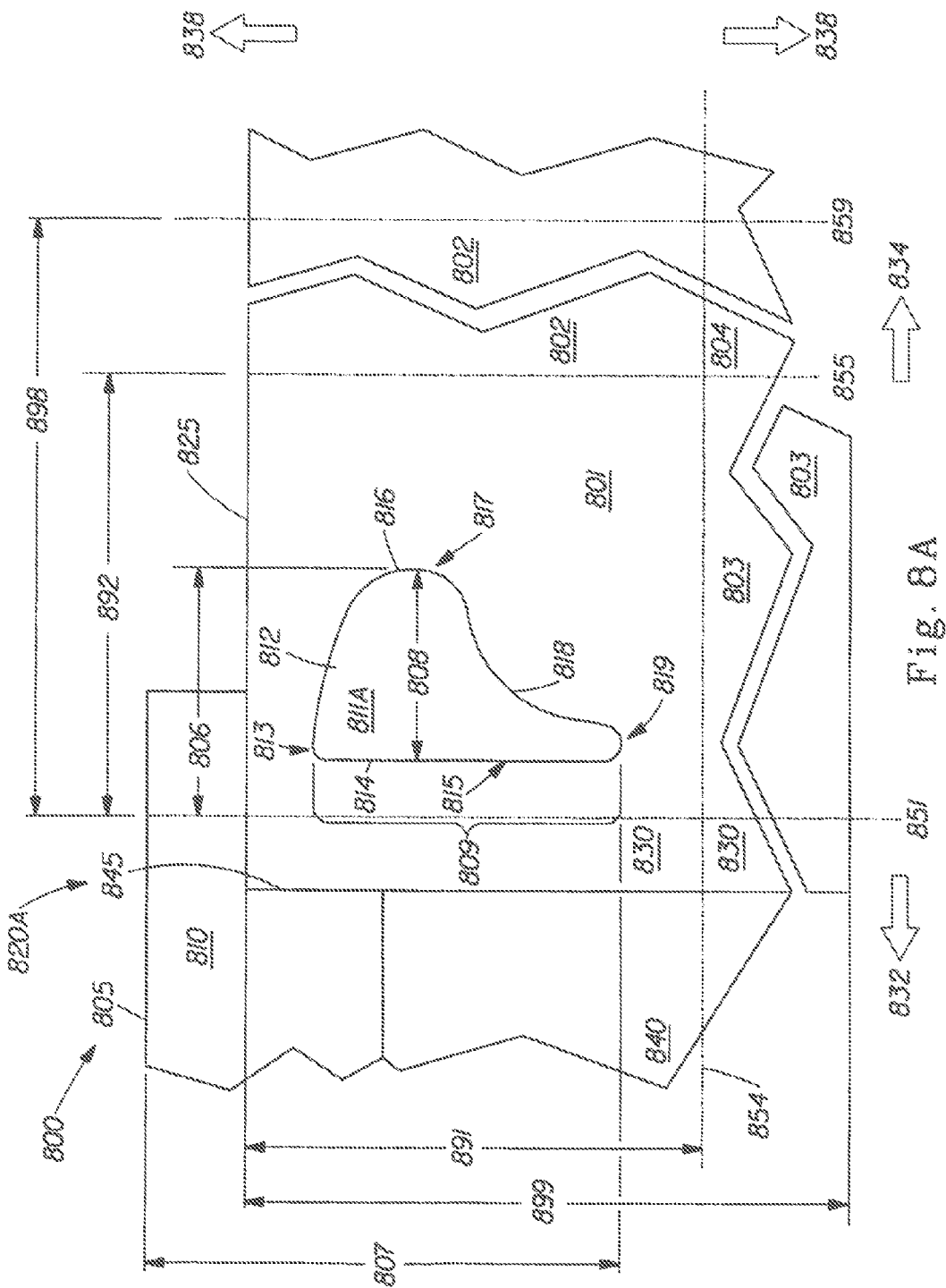
FIG. 8A illustrates a top view of an embodiment of a high modulus region in a first area of a substantially laterally extensible area of an extensible side of a disposable wearable absorbent article according to embodiments of the present disclosure.

Throughout the present disclosure, the term "like-numbered" is intended to illustrate a correspondence between labels of elements wherein the last two numbers in the labels of the elements are the same. Element labels are considered to be like-numbered despite differing numeral prefixes corresponding to figure numbers. For example, for the back waist edge 605 of the embodiment of FIG. 6, the back waist edge 505 of the embodiment of FIG. 5 is a like-numbered element. Also, element labels are considered to be like-numbered despite differing alphabetical suffixes corresponding to particular embodiments. As an example, for the extensible side 920B of the embodiment of FIG. 9B, the extensible side 820A of the embodiment of FIG. 8A is a like-numbered element.

FIG. 6 further includes arrows indicating relative directions for laterally inboard 632, laterally outboard 634, longitudinally inboard 636, and longitudinally outboard 638, with respect to the disposable wearable absorbent article 600.

Since the side panel 620 is connected to the back 640 and the front 660 of the disposable wearable absorbent article 600, the side panel 620 can relate to a lateral centerline of the article 600 at the back 640 and the front 660, as will be understood by one of ordinary skill in the art. For ease of reference, FIG. 6 illustrates relative lateral directions for the extensible side panel 620, by relating the extensible side panel 620 to the lateral centerline of the article 600 at the back 640 and not the front 660. Descriptions connected with the embodiment of FIG. 6, also refer to relative lateral directions for the extensible side panel 620, by relating the extensible side panel 620 to the lateral centerline of the article 600 at the back 640 and not the front 660. These illustrations and descriptions for relative lateral directions are used for embodiments of extensible side panels throughout the present disclosure, unless otherwise indicated.

In various embodiments, a tensile force can be generated in an extensible side of a disposable wearable absorbent article. As an example, a tensile force can be generated in an extensible side ear of a disposable wearable absorbent article, such as the side ear 520 of the embodiment of FIG. 5, when refastenably connecting the extensible side ear to a front of the disposable wearable absorbent article. Also as an example, a tensile force can be generated in an extensible side panel of a disposable wearable absorbent article, such as the side panel 620 of the embodiment of FIG. 6, when the extensible side panel is worn by a wearer. Such tensile forces can extend a substantially laterally extensible area in the extensible side, from an original lateral dimension to an extended lateral dimension.

Where an overall lateral extensibility of a first area is substantially less than an overall lateral extensibility of one or more other areas in the substantially laterally extensible area, as described in connection with embodiments of FIG. 7A, the first area can extend substantially less than those other areas when the extensible side is subjected to the same tensile force. Throughout this disclosure, the term "substantially," when used to describe a relative quantitative difference (e.g. substantially greater than or substantially less than), refers to a difference of at least 25%, unless otherwise indicated. While not wishing to be bound by this theory, it is believed that, in these embodiments, tensile forces can be directed through the first area of the extensible side to an upper portion of the article proximate to a waist edge. Thus, a disposable wearable absorbent article with extensible sides of the present disclosure can create greater tension in upper portions of the extensible sides helping the article to fit snugly, stay in place, and not leak, while still allowing the extensible sides to extend with reasonably low forces for easy application.

FIG. 7A is a chart illustrating various relationships of lateral extensibilities for areas of a substantially laterally extensible area of an extensible side of a disposable wearable absorbent article according to embodiments of the present disclosure. The rows labeled 1 through 8 refer to embodiments of the present disclosure. The columns labeled A1 through A4 refer to the areas of the substantially laterally extensible area. The label A1 refers to a first area of the substantially laterally extensible area, such as the first area 501 of the side ear 520 or the first area 601 of the side panel 620. The label A2 refers to a second area of the substantially laterally extensible area, such as the second area 502 of the side ear 520 or the second area 602 of the side panel 620. The label A3 refers to a third area of the substantially laterally extensible area, such as the third area 503 of the side ear 520 or the third area 603 of the side panel 620. The label A4 refers to a fourth area of the substantially laterally extensible area, such as the fourth area 504 of the side ear 520 or the fourth area 604 of the side panel 620. The label Aall refers to all of the areas (A1, A2, A3, and A4) of the substantially laterally extensible area taken together as a collective whole. In the chart of FIG. 7A, cells formed by the rows and the columns contain information about the overall lateral extensibilities of A1, A2, A3, and A4 in the embodiments 1 through 8.

In the first embodiment of the chart of FIG. 7A, the relationships of the areas are described with respect to A1. In this first embodiment, an overall lateral extensibility of the first area is substantially less than an overall lateral extensibility of all of the areas as a collective whole.

In the second embodiment of the chart of FIG. 7A, the relationships of the areas are described with respect to A1. In this second embodiment, an overall lateral extensibility of the first area is substantially less than an overall lateral extensibility of each of the following: the second area, the third area, the fourth area, and all of the areas as a collective whole.

In the third embodiment of the chart of FIG. 7A, the relationships of the areas are described with respect to A1 and A2. In this third embodiment, an overall lateral extensibility of the first area is substantially less than an overall lateral extensibility of each of the following: the second area, the third area, the fourth area, and all of the areas as a collective whole. Also in this third embodiment, an overall lateral extensibility of the second area is substantially equal to an overall lateral extensibility of each of the following: the third area and the fourth area.

In the fourth embodiment of the chart of FIG. 7A, the relationships of the areas are described with respect to A1 and A2. In this fourth embodiment, an overall lateral extensibility of the first area is substantially less than an overall lateral extensibility of each of the following: the second area, the third area, the fourth area, and all of the areas as a collective whole. Also in this fourth embodiment, an overall lateral extensibility of the second area is substantially less than an overall lateral extensibility of each of the following: the third area and the fourth area.

In the fifth embodiment of the chart of FIG. 7A, the relationships of the areas are described with respect to A1, A2, and A4. In this fifth embodiment, an overall lateral extensibility of the first area is substantially less than an overall lateral extensibility of each of the following: the second area, the third area, the fourth area, and all of the areas as a collective whole. Also in this fifth embodiment, an overall lateral extensibility of the second area is substantially less than an overall lateral extensibility of the third area. Further, in this fifth embodiment, an overall lateral extensibility of the fourth area is substantially less than an overall lateral extensibility of the third area.

In the sixth embodiment of the chart of FIG. 7A, the relationships of the areas are described with respect to A1 and A4. In this sixth embodiment, an overall lateral extensibility of the first area is substantially less than an overall lateral extensibility of each of the following: the second area, the third area, the fourth area, and all of the areas as a collective whole. Also in this sixth embodiment, an overall lateral extensibility of the fourth area is substantially less than an overall lateral extensibility of each of the following: the second area and the third area.

In the seventh embodiment of the chart of FIG. 7A, the relationships of the areas are described with respect to A1 and A3. In this seventh embodiment, an overall lateral extensibility of the first area is substantially less than an overall lateral extensibility of each of the following: the second area, the third area, the fourth area, and all of the areas as a collective whole. Also in this seventh embodiment, an overall lateral extensibility of the third area is substantially less than an overall lateral extensibility of the second area.

In the eighth embodiment of the chart of FIG. 7A, the relationships of the areas are described with respect to A1 and A3. In this eighth embodiment, an overall lateral extensibility of the first area is substantially less than an overall lateral extensibility of each of the following: the second area, the third area, the fourth area, and all of the areas as a collective whole. Also in this eighth embodiment, an overall lateral extensibility of the third area is substantially less than an overall lateral extensibility of the fourth area. In addition to the eight embodiments described in the embodiment of FIG. 7A, a substantially laterally extensible area of an extensible side of a disposable wearable absorbent article can be configured with various additional lateral extensibilities, such that a first area can extend substantially less than other areas in the substantially laterally extensible area when the extensible side is subjected to a tensile force, as will be understood by one of ordinary skill in the art. A first area can also be configured with various lateral extensibilities by using combinations of part or all or any configurations for a first area described in the present disclosure.

Figure 7B:
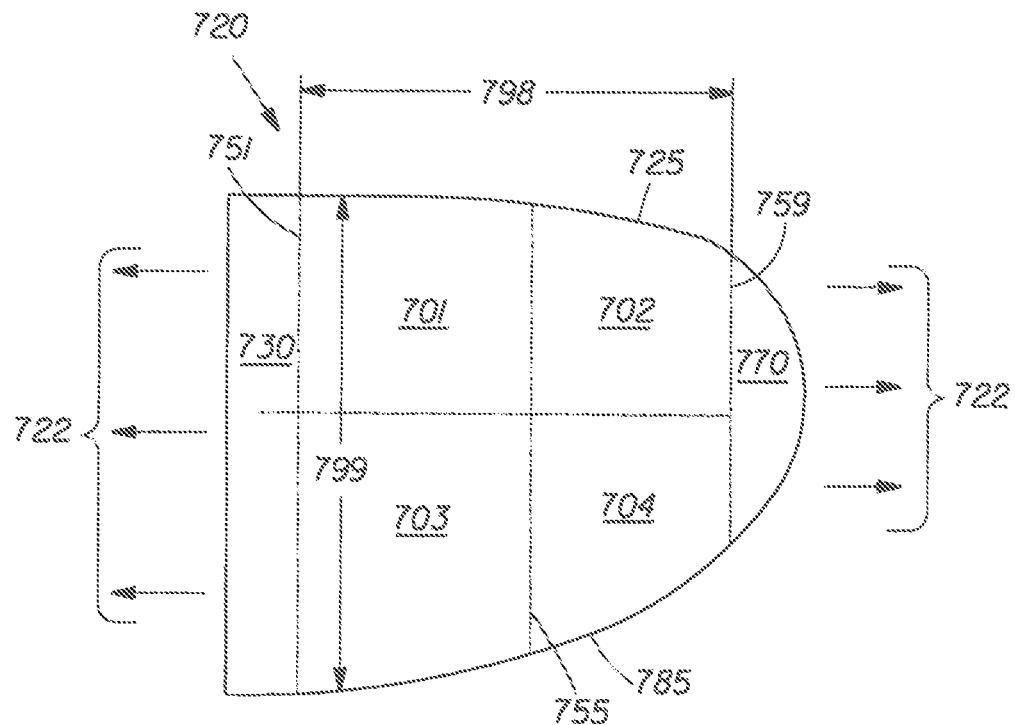
FIG. 7B illustrates a top view of an embodiment of an extensible side ear of a disposable wearable absorbent article, for use in testing, according to the present disclosure.

FIG. 7B illustrates a top view of an embodiment of an extensible side ear 720 separated from a disposable wearable absorbent article, for use in testing, according to the present disclosure. The extensible side ear 720 includes a substantially laterally extensible area, which includes a first area 701, a second area 702, a third area 703, and a fourth area 704. The extensible side ear 720 also includes a longitudinally outboard side edge 725, a laterally inboard margin 730, a first lateral reference line 751, a second lateral reference line 755, a third lateral reference line 759, a laterally outboard margin 770, a longitudinally inboard side edge 785, an overall area lateral width 798, and an overall area longitudinal length 799. In various embodiments, the extensible side ear 720 can be the extensible side ear 520 of the embodiment of FIG. 5 and one or more of the elements of the embodiment of FIG. 7 can be the like-numbered element of the embodiment of FIG. 5.

Test Method for a Substantially Laterally Extensible Area Taken as a Collective Whole The extensible side ear 720 can be tested to determine a force to laterally extend the substantially laterally extensible area to one or more particular laterally extended dimensions. This test method can also be adapted for used with a side panel, as will be understood by one of ordinary skill in the art. A force to laterally extend can be used as an indicator of lateral extensibility. If a substantially laterally extensible area has a relatively high force to laterally extend, then the substantially laterally extensible area can be considered to have a relatively low lateral extensibility (e.g. difficult to laterally extend). If a substantially laterally extensible area has a relatively low force to laterally extend, then the substantially laterally extensible area can be considered to have a relatively high lateral extensibility (e.g. easy to laterally extend). Thus, the extensible side ear 720 can be tested to determine a force to laterally extend the substantially laterally extensible area, which can be used to indicate an overall lateral extensibility of the area.

FIG. 7B further includes arrows indicating directions of equal and opposite lateral extension forces 722, which can be generated in the side ear 720 during testing. These arrows are intended to illustrate the directions of the extension forces 722, and are not intended to illustrate any particular magnitude or distribution of the extension forces 722. The extensible side ear 720 of the embodiment of FIG. 7B can be tested to determine a force to laterally extend the areas 701, 702, 703, and 704, taken together as a collective whole. The force to laterally extend can be determined by measuring the forces used to laterally extend the substantially laterally extensible area to one or more particular lateral extensions. These forces can be measured in various ways, such as by using a tensile testing machine.

To perform this testing, the extensible side ear 720 can be placed in grips of a tensile testing machine in an unextended state. The extensible side ear 720 can be gripped in various ways to isolate the substantially laterally extensible area, to facilitate substantially lateral extensions, to distribute tensile forces longitudinally, and to reduce out-of-plane buckling as the extensible side ear 720 is laterally extended under tension. The extensible side ear 720 can be gripped in the laterally inboard margin 730, immediately laterally inboard to the first lateral reference line 751 with a first grip extending over the entire overall area longitudinal length 799 and gripped in the laterally outboard margin 770, immediately laterally outboard from the third lateral reference line 759 with a second grip extending over the entire longitudinal length of the laterally outboard margin 770.

Further, in this example, once the extensible side ear 720 is placed in the grips, the tensile testing machine can move one or both of the grips at one or more particular rates, so that the substantially laterally extensible area of the extensible side ear 720 is substantially laterally extended. The tensile testing machine can measure forces used to laterally extend the substantially laterally extensible area to one or more particular lateral extensions. In this example, the tensile testing machine can measure forces used to laterally extend the substantially laterally extensible area in size from the original overall area lateral width 798 dimension to laterally extended dimensions 50%, 100%, and 150% greater than the overall area lateral width 798. The forces used by the tensile testing machine can be measured at each of these laterally extended dimensions. For instance, the forces can be measured by using a load cell in the tensile testing machine.

Thus, such testing can yield data for the force to laterally extend the substantially laterally extensible area of the extensible side ear 720. This data can be expressed in units of force, at laterally extended dimensions expressed as percentages of increase in size over the original lateral dimension. For example, a datum can be 2 Newtons of force at a 150% laterally extended dimension. The force used to laterally extend the substantially laterally extensible area depends at least in part on the longitudinal length of the substantially laterally extensible area. In order to account for this effect, each of the force data can be divided by the overall area longitudinal length 799, resulting in data with units of force divided by a length dimension. Using the previous example, for an overall area longitudinal length of 2 centimeters, the datum can be 1 Newton of force per centimeter at a 150% laterally extended dimension (e.g. 1 N/cm at 150%). This testing can also be adapted for use with extensible side panels, to determine a force to laterally extend the areas in a side panel, taken together as a collective whole, as will be understood by one of ordinary skill in the art. Similar testing can be performed on a portion of the extensible side ear 720, as described in connection with the embodiment of FIG. 7C.

In various embodiments, the substantially laterally extensible area of the extensible side ear 720 can be configured to extend easily so that a disposable wearable absorbent article that includes the extensible side ear 720 can be easily applied to and/or fastened on a wearer. In order to provide for this ease of application and/or fastening, the substantially laterally extensible area of the extensible side ear 720 can be configured in various embodiments to have a force to laterally extend, which is less than 5 N/cm, or less than 2 N/cm, or less than 1.5 N/cm, or even less than 1 N/cm at 50%, 100%, or even at 150% laterally extended dimensions. The substantially laterally extensible area of the extensible side ear 720 can be configured to have a low force to laterally extend (e.g. easy to laterally extend), even when one or more areas in the substantially laterally extensible area are configured to have a relatively greater force to laterally extend (e.g. more difficult to laterally extend), as described in connection with the embodiments of FIG. 7A.

Figure 7C:
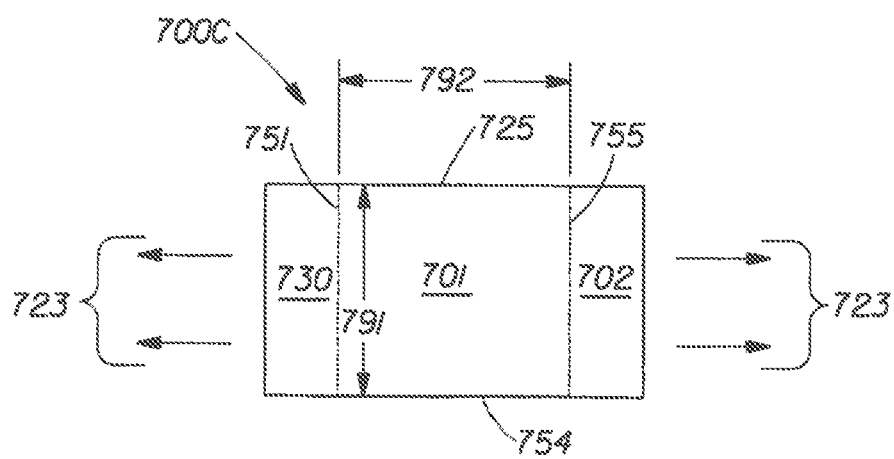
FIG. 7C illustrates a top view of an embodiment of a portion of the extensible side ear of FIG. 7B, for use in testing, according to the present disclosure.

FIG. 7C illustrates a top view of an embodiment of a portion 700C separated from the extensible side ear 720 of FIG. 7B, for use in testing, according to the present disclosure. The portion 700C is cut from the extensible side ear 720. The portion 700C includes the first area 701, a portion of the second area 702, a portion of the longitudinally outboard side edge 725, a portion of the laterally inboard margin 730, a portion of the first lateral reference line 751, a portion of the third lateral reference line 759, a first lateral width 792, and a first area longitudinal length 791.

Test Method for an Area in a Substantially Laterally Extensible Area

The portion 700C can be tested to determine a force to laterally extend the first area 701 to one or more particular laterally extended dimensions. This test method can also be adapted for used with a side panel, as will be understood by one of ordinary skill in the art. As described above, a force to laterally extend can be used as an indicator of lateral extensibility. Thus, the portion 700C can be tested to determine a force to laterally extend the first area 701, which can be used to indicate an overall lateral extensibility of the first area 701.

FIG. 7C further includes arrows indicating directions of equal and opposite lateral extension forces 723, which can be generated in the portion 700C of the extensible side ear 720 during testing. These arrows are intended to illustrate the directions of the extension forces 723, and are not intended to illustrate any particular magnitude or distribution of the extension forces 723. The portion 700C of the embodiment of FIG. 7C can be tested to determine a force to laterally extend the first area 701. The force to laterally extend can be determined by measuring the forces used to laterally extend the first area 701 to one or more particular lateral extensions. These forces can be measured in various ways, such as by using a tensile testing machine.

To perform the testing, the portion 700C of the extensible side ear 720 can be placed in grips of a tensile testing machine in an unextended state. The portion 700C can be gripped in various ways to isolate the area 701, to facilitate substantially lateral extensions, to distribute tensile forces longitudinally, and to reduce out-of-plane buckling as the first area 701 is laterally extended under tension. The portion 700C can be gripped in the portion of the laterally inboard margin 730, immediately laterally inboard to the first lateral reference line 751 with a first grip extending over the entire first area longitudinal length 791 and gripped in the portion of the laterally outboard margin 770, immediately laterally outboard from the third lateral reference line 759 with a second grip extending over the entire longitudinal length of the portion of the portion of the second area 702.

Further, in this example, once the portion 700C of the extensible side ear 720 is placed in the grips, the tensile testing machine can move one or both of the grips at one or more particular rates, so that the first area 701 of the portion 700C is substantially laterally extended. The tensile testing machine can measure forces used to laterally extend the first area 701 to one or more particular lateral extensions. In this example, the tensile testing machine can measure forces used to laterally extend the area 701 in size from the original first lateral width 792 dimension to laterally extended dimensions 50%, 100%, and 150% greater than the first lateral width 792. The forces used by the tensile testing machine can be measured at each of these laterally extended dimensions, as described in connection with the embodiment of FIG. 7B.

Thus, such testing can yield data for the force to laterally extend the first area 701. This data can be expressed in units of force, at laterally extended dimensions expressed as percentages of increase in size over the original lateral dimension. As described in connection with the embodiment of FIG. 7B, each of the force data can be divided by the first area longitudinal length 791, resulting in data with units of force divided by a length dimension. Similar testing can be performed on individual areas 702, 703, or 704, or on individual areas from an extensible side panel. For testing of these individual areas, each of the force data can be divided by a longitudinal length of a laterally inboard portion of a boundary of the area, as described in connection with the embodiment of FIG. 5.

By using data yielded from testing, as described in connection with embodiments of FIGS. 7B and/or 7C, various forces to laterally extend can be compared. Forces to laterally extend should be compared at the same particular laterally extended dimensions, when the laterally extended dimensions are expressed as percentages of increase in size over original lateral dimensions. For example, a force to laterally extend the first area 701 to a 50% laterally extended dimension should be compared with a force to laterally extend the substantially laterally extensible area of FIG. 7B to a 50% laterally extended dimension. Also as an example, a force to laterally extend the first area 701 to a 50% laterally extended dimension should be compared with a force to laterally extend the second area 702, the third area 703, or the fourth area 704 to a 50% laterally extended dimension. Similarly, forces to laterally extend should be compared at laterally extended dimensions of 100%, 150%, or other particular laterally extended dimensions, as will be understood by one of ordinary skill in the art.

In some embodiments, a comparison of forces to laterally extend can be expressed in the form of a force ratio. A force ratio compares forces to laterally extend two different areas from the same substantially laterally extensible area. For example, a force to laterally extend a first area, such as the first area 701, can be divided by a force to laterally extend a second area, such as the second area 702, to obtain a force ratio relating the first area 701 to the second area 702. Since the force to laterally extend each of the two areas can be expressed as units of force divided by a length dimension, these units can cancel to yield a dimensionless ratio. In various embodiments, a first area in a substantially laterally extensible area, such as the first area 701, can have a force ratio greater than about 1.25, greater than about 1.5, or even greater than about 1.7, when relating the first area to a second area, a third area, or a fourth area, in the substantially laterally extensible area, when compared at the same particular laterally extended dimensions, such as 50%, 100%, 150%, or other particular laterally extended dimension.

A force ratio can also compare a force to laterally extend one area in a substantially laterally extensible area to a force to laterally extend the substantially laterally extensible area. For example, a force to laterally extend a first area, such as the first area 701, can be divided by a force to laterally extend a substantially laterally extensible area that includes the first area along with a second area, a third area, and a fourth area, such as the areas 702, 703, and 704. The force ratio can be dimensionless as described above. In various embodiments, a first area in a substantially laterally extensible area, such as the first area 701, can have a force ratio greater than about 1.25, greater than about 1.5, or even greater than about 1.7, when relating the first area to a substantially laterally extensible area that includes the first area along with a second area, a third area, and a fourth area, when compared at the same particular laterally extended dimensions, such as 50%, 100%, 150%, or other particular laterally extended dimension. Extensible sides can be configured in a number of ways to achieve various forces to laterally extend as described in connection with the embodiments of FIGS. 8 through 16B.

As examples of the testing described above, force ratios were measured for side ears from current market Pampers™ Cruisers™ products and from side ears of a test sample, configured according to embodiments of the present disclosure. In the tables, the labels A1, A2, A3, A4, and Aall refer to a first, a second area, a third area, a fourth area, and a substantially laterally extensible area, as described in connection with the embodiment of FIG. 7A.

Table 1, provided below, contains data from the testing of the side ears of current market Pampers™ Cruisers™ products.

TABLE 1

| Area | force per length (N/cm) at various strains (%) | | | force ratio compared to A1 at various strains (%) | | |
|---|---|---|---|---|---|---|
| | 50% | 100% | 150% | 50% | 100% | 150% |
| A1 | 0.67 | 1.03 | 1.75 | 1.0 | 1.0 | 1.0 |
| A2 | 0.63 | 1.0 | 1.78 | 1.06 | 1.02 | 0.98 |
| A3 | 0.57 | 0.87 | 1.44 | 1.18 | 1.18 | 1.22 |
| A4 | 0.61 | 0.95 | 1.68 | 1.11 | 1.07 | 1.04 |
| Aall | 0.56 | 0.89 | 1.61 | 1.2 | 1.15 | 1.09 |

As shown in Table 1, the force ratios ranged from 0.98 to about 1.22.

Table 2, provided below contains data from the testing of the side ears of the test product, which included a high modulus region in the first area as described herein.

TABLE 2

| Area | force per length (N/cm) at various strains (%) | | | force ratio compared to A1 at various strains (%) | | |
|---|---|---|---|---|---|---|
| | 50% | 100% | 150% | 50% | 100% | 150% |
| A1 | 0.83 | 1.42 | 2.15 | 1.0 | 1.0 | 1.0 |
| A2 | 0.66 | 0.86 | 1.1 | 1.27 | 1.66 | 1.96 |
| A3 | 0.66 | 0.86 | 1.09 | 1.27 | 1.64 | 1.97 |
| A4 | 0.59 | 0.82 | 1.06 | 1.4 | 1.74 | 2.04 |
| Aall | 0.61 | 0.86 | 1.25 | 1.36 | 1.66 | 1.72 |

As shown in Table 2, the force ratios ranged from 1.27 to 2.04. Thus, as shown by the data in Tables 1 and 2, a substantially laterally extensible area of an extensible side of a disposable wearable absorbent article can be configured such that an overall lateral extensibility of a first area can be substantially less than an overall lateral extensibility of some and/or all of other areas in the substantially laterally extensible area.

FIG. 8A illustrates a top view of an embodiment of a high modulus region 811A in a first area 801 of a substantially laterally extensible area of an extensible side 820A of a disposable wearable absorbent article 800 according to embodiments of the present disclosure. In FIG. 8A, the extensible side 820A and the disposable wearable absorbent article 800 are illustrated in part. The extensible side 820A is connected to a back 840 of the disposable wearable absorbent article 800. FIG. 8A also illustrates a back waist edge 805 and a back upper portion 810 of the disposable wearable absorbent article 800.

The extensible side 820A includes the first area 801, a second area 802, a third area 803, and a fourth area 804, with area 802 illustrated in part and areas 803 and 804 illustrated in broken part. The first area 801 includes the high modulus region 811A. For clarity, in the embodiments of FIGS. 8A, 9A-13A, 15A, and 16A, high modulus regions are illustrated as visibly apparent elements within side panels and side ears. However, in various embodiments, part or all of a high modulus region may not be readily visibly apparent within a disposable wearable absorbent article.

The high modulus region 811A includes a widest lateral dimension 808 and a longest longitudinal dimension 809. The embodiment of FIG. 8A also includes a high modulus region lateral offset 806 and high modulus region longitudinal offset 807. The high modulus region 811A further includes a longitudinally outboard region edge 812 with a furthest longitudinally outboard point 813, a laterally inboard region edge 814 with a furthest laterally inboard point 815, a laterally outboard region edge 816 with a furthest laterally outboard point 817, and a longitudinally inboard region edge 818 with a furthest longitudinally inboard point 819. The extensible side 820A also includes a longitudinally outboard side edge 825, a laterally inboard margin 830, and a laterally inboard side edge 845. The embodiment of FIG. 8A includes a first lateral reference line 851, a longitudinal reference line 854, a second lateral reference line 855, a third lateral reference line, a first area longitudinal length 891, a first lateral width 892, an overall area lateral width 898, and an overall area longitudinal length 899.

FIG. 8A further includes arrows indicating relative directions for laterally inboard 832, laterally outboard 834, longitudinally inboard 836, and longitudinally outboard 838, with respect to the disposable wearable absorbent article 800. In various embodiments, the extensible side 820A can be the extensible side ear 520 of the embodiment of FIG. 5 and one or more of the elements of the embodiment of FIG. 8A can be the like-numbered element of the embodiment of FIG. 5. Also, in various embodiments, the extensible side 820A can be the extensible side panel 620 of the embodiment of FIG. 6 and one or more of the elements of the embodiment of FIG. 8A can be the like-numbered element of the embodiment of FIG. 6.

In the embodiment of FIG. 8A, the high modulus region 811A is located within the first area 801. In various embodiments, the high modulus region 811A can be located in various parts of the first area 801. In the embodiment of FIG. 8A, the high modulus region 811A occupies part of the first area 801, although, in various embodiments, the high modulus region 811A can occupy one or more parts or all of the first area 801. In some embodiments, one or more portions of the high modulus region 811A can extend into one or more of the second area 802, the third area 803, and/or the fourth area 804.

The high modulus region 811A is bounded by a region boundary including the longitudinally outboard region edge 812, the laterally inboard region edge 814, the laterally outboard region edge 816, and the longitudinally inboard region edge 818. In the embodiment of FIG. 8A, the high modulus region 811A is offset from the longitudinally outboard side edge 825 and also offset from the laterally inboard side edge 845. Part or all of the region boundary can, in some embodiments, coincide with part or all of one or more of the side edges and/or the reference lines, for example as illustrated in the embodiments of FIGS. 9 and 10.

In the embodiment of FIG. 8A, the region boundary of the high modulus region 811A has an overall tear-drop shape, however, in various embodiments the overall shape of a region boundary can be various shapes, such as a square, rectangle, triangle, trapezoid, octagon, hexagon, star, half circle, a quarter circle, a half oval, a quarter oval, a radial pattern, and other shapes. In various embodiments, the overall shape of a region boundary can be a recognizable image, such as a letter, a number, a word, or a character (such as a face of an animal or person) or other recognizable image (such as a plant, a car, etc.). An overall shape of a region boundary can be rounded in various embodiments, to reduce the potential for creating stress concentrations at the region boundary.

Also, in some embodiments, a high modulus region can include one or more regions within a region boundary with a relatively lower lateral modulus of elasticity. For example, a high modulus region can be configured as a series of dots arranged in an overall shape, such as a circle, wherein the area of each dot has a greater lateral modulus of elasticity than surrounding portions of the substantially laterally extensible that are outside of the high modulus region. In this way, the dots form a high modulus region that effectively constrains areas within the region boundary.

Dimensions related to high modulus region 811A can be measured in various ways. The widest lateral dimension 808 is a width measured from the furthest laterally inboard point 815 to the furthest laterally outboard point 817. In some embodiments, including the embodiment of FIG. 8A, the widest lateral dimension 808 of the high modulus region 811A can be disposed within the first area 801, proximate to the longitudinally outboard side edge 825. The longest longitudinal dimension 809 can be measured from the furthest longitudinally outboard point 813 to the furthest longitudinally inboard point 819. In some embodiments, including the embodiment of FIG. 8A, the longest longitudinal dimension 809 of the high modulus region 811A can be disposed within the first area 801, proximate to the laterally inboard side edge 845.

The high modulus region longitudinal offset 807 can be measured longitudinally from the furthest longitudinally inboard point 819 to the back waist edge 805. The high modulus region longitudinal offset 807 can, in various embodiments, be configured to be less than or equal to fifteen percent of a pitch of the disposable wearable absorbent article 800 to which the extensible side 820A is attached. In some embodiments, the high modulus region longitudinal offset 807 can be configured to be less than or equal to ten percent or even less than or equal to five percent of a pitch of the disposable wearable absorbent article 800 to which the extensible side 820A is attached. Thus, the longitudinal position of the high modulus region 811A in the disposable wearable absorbent article 800 can be configured to change in proportion to the pitch of the article.

By configuring the high modulus region longitudinal offset 807 to change in proportion to the pitch of the article, the high modulus region 811A can be disposed within the extensible side 820A above a PHIP of the wearer, even with a shortened pitch. In this way, the high modulus region 811A can also create greater tension in upper portions of the extensible side 820A, allowing the extensible sides to extend easily and helping the article to fit snugly, stay in place, and not leak.

The high modulus region lateral offset 806 can be measured laterally from the furthest laterally outboard point 817 to the first lateral reference line 851. In various embodiments, the high modulus region lateral offset 806 and/or the widest lateral dimension 808 can relate to the first lateral width 892 and/or the overall area lateral width 898 in various ratios. In some embodiments, the ratio of the high modulus region lateral offset 806 to the first lateral width 892 can be less than or equal to 1.5, or less than or equal to 1.0, or less than or equal to 0.85, or even less than or equal to 0.5 and the ratio of the high modulus region lateral offset 806 to the overall area lateral width 898 can be less than or equal to 0.75, or less than or equal to 0.5 (e.g. 0.43), or even less than or equal to 0.4. Also, in some embodiments, the ratio of the widest lateral dimension 808 to the first lateral width 892 can be less than or equal to 1.5, or less than or equal to 1.0, or less than or equal to 0.85, or even less than or equal to 0.5 and the ratio of the widest lateral dimension 808 to the overall area lateral width 898 can be less than or equal to 0.75, or less than or equal to 0.5, (e.g. 0.43), or even less than or equal to 0.4. Thus, the lateral position of the high modulus region 811A in the extensible side 820A can be configured to change in proportion to lateral dimensions of the substantially lateral extensible area.

In various embodiments, the longest longitudinal dimension 809 can relate to the first area longitudinal length 891 and/or the overall area longitudinal length 899 in various ratios. In some embodiments, the ratio of the longest longitudinal dimension 809 to the first area longitudinal length 891 can be less than or equal to 1.5, or less than or equal to 1.0, or less than or equal to 0.85, or even less than or equal to 0.5 (e.g. 0.48). Also, in some embodiments, the ratio of the longest longitudinal dimension 809 to the overall area longitudinal length 899 can be less than or equal to 0.75, or less than or equal to 0.5, or even less than or equal to 0.4 (e.g. 0.24). Thus, the longest longitudinal dimension 809 of the high modulus region 811A in the extensible side 820A can be configured to change in proportion to longitudinal dimensions of the substantially lateral extensible area.

The high modulus region 811A can be configured in various ways, to provide an overall lateral extensibility in the first area 801 that is substantially less than an overall lateral extensibility of one or more other areas in the substantially laterally extensible area, as described in connection with embodiments of FIG. 7A. First, the high modulus region 811A can be configured to have a particular overall lateral extensibility that is substantially less than an overall lateral extensibility of one or more portions of the substantially laterally extensible that are outside of the high modulus region 811A. Thus, the one or more portions of the substantially laterally extensible that are outside of the high modulus region 811A can have an overall lateral extensibility that is substantially greater than the particular overall lateral extensibility of the high modulus region 811A. In some embodiments of this first configuration, these one or more portions outside of the high modulus region 811A can cover a majority of the substantially laterally extensible area.

Second, the high modulus region 811A can be configured to have a particular overall lateral modulus of elasticity that is substantially greater than an overall lateral modulus of elasticity of one or more portions of the substantially laterally extensible that are outside of the high modulus region 811A. Thus, the one or more portions of the substantially laterally extensible that are outside of the high modulus region 811A can have an overall lateral modulus of elasticity that is substantially less than the particular overall lateral extensibility of the high modulus region 811A. In some embodiments of this second configuration, these one or more portions outside of the high modulus region 811A can cover a majority of the substantially laterally extensible area.

The first and/or the second configurations of the high modulus region 811A, described above, can be implemented in various ways, as described in the following examples. As a first example, one or more portions of the substantially laterally extensible area that are outside of the high modulus region 811A can include one or more particular materials, which are bonded together to a particular lesser degree of bonding, and part or all of the high modulus region 811A can include these particular materials, which are bonded together to a particular greater degree of bonding. A greater degree of bonding can be obtained in the high modulus region 811A by fusing together material in part or all of the high modulus region 811A and/or by adding one or more adhesives, bonding agents, and/or polymers to part or all of the high modulus region 811A. Such adhesives, bonding agents, and/or polymers can be added externally to a surface of the substantially laterally extensible area and/or internally between one or more layers of material (e.g. laminate material) of the substantially laterally extensible area, as described in connection with embodiment of FIG. 8H. Fusing can be accomplished in various ways, such as by thermal bonding, pressure bonding, ultrasonic bonding, etc. For instance, a substantially laterally extensible area can be mechanically activated, thus breaking fibers apart, and a high modulus region can be formed by at least partially bonding fibers back together in a portion of the substantially laterally extensible area.

As a second example, one or more portions of the substantially laterally extensible area that are outside of the high modulus region 811A can include one or more particular materials, and part or all of the high modulus region 811A can include these particular materials and a layer of an additional material, connected to the high modulus region 811A. The additional material can, in some embodiments, be substantially laterally inextensible or can have a relatively high lateral modulus of elasticity. As examples, the additional material can be a piece of nonwoven, film, foam, scrim mesh, or other solid form. The additional material can be fused or bonded to the high modulus region 811A. Alternatively, the additional material can be a substrate, formed from a material, such as a liquid polymer (e.g. polypropylene, polyethylene, and/or polyethylene terephthalate), adhesive, or wax, which can solidify after being applied to the high modulus region 811A in liquid form. The additional material can be added externally to a surface of the substantially laterally extensible area, as described in connection with embodiment of FIG. 8I.

As a third example, one or more portions of the substantially laterally extensible area that are outside of the high modulus region 811A can include one or more particular materials, which together have a particular lesser thickness, and part or all of the high modulus region 811A can include these particular materials, which together have a particular greater thickness. As further examples, high modulus region 811A can be configured to have a lesser overall lateral extensibility and/or a greater overall lateral modulus of elasticity, when compared with one or more portions of the substantially laterally extensible that are outside of the high modulus region 811A, by utilizing materials with differential mass, thickness, and/or modulus of elasticity (via different thermoplastic printing, printing patterns, laydown chemistries, etc.) as described in U.S. Publication No. US 2007-0142815, filed Dec. 16, 2005, and entitled "Force Focused Fastening Member." A high modulus region can also be configured by using combinations of part or all of these examples and/or any other configurations for a high modulus region described in the present disclosure.

Modulus Mapping Test Method for Detecting High Modulus Region

FIG. 8B illustrates a perspective view of a disposable wearable absorbent article 800B with extensible side ears 820B, formed for wearing, according to embodiments of the present disclosure. The disposable wearable absorbent article 800B includes a front waist edge 805, a front upper portion 810, the extensible side ears 820B, a back 840, a front 860, a back upper portion 890, and a back waist edge 895.

The extensible side ears 820B are configured to connect the front 860 and the back 840 of the absorbent article 800B. In the embodiment of FIG. 8B, the extensible side ears 820B are durably connected to the back 840 and refastenably connected to the front 860. The disposable wearable absorbent article 800B is an embodiment of the disposable wearable absorbent article 800A of the embodiment of FIG. 8A.

The extensible side ear 820B includes a substantially laterally extensible area and a high modulus region. In the embodiment of FIG. 8B, the substantially laterally extensible area and the high modulus region are not readily visibly apparent, and thus are not shown in FIG. 8B. However, the extent of a substantially laterally extensible area and the presence of a high modulus region can be determined and detected by using a modulus mapping method. This method can also be used to measure particular modulus of elasticity values for areas within the extensible side ear 820B, such as a high modulus region. This test method can also be adapted for used with a side panel, as will be understood by one of ordinary skill in the art. The modulus mapping method is described below, and in connection with the embodiments of FIGS. 8C-8G.

A first step in the modulus mapping method is to determine an area of interest in a disposable wearable absorbent article. The area of interest is a continuous portion of the article, which completely contains the substantially laterally extensible area and the high modulus region to be tested. The area of interest also includes one or more portions of the article surrounding the substantially laterally extensible area and the high modulus region. In other words, the area of interest is not limited to the area and the region, but includes the one or more portions of the article that form the physical context on all available sides of the substantially laterally extensible area and the high modulus region. The area of interest should contain enough of this physical context to be tested with the modulus mapping method on all sides of the area and the region. In this way, the extent of the substantially laterally extensible area and the presence of the high modulus region can be determined and detected within their physical context, in the area of interest.

The extent of a substantially laterally extensible area and/or the presence of a high modulus region may be known from knowledge of the article. In the embodiment of FIG. 8B, since the extensible side ear 820B is known to contain a high modulus region within a substantially laterally extensible area, the extensible side ear 820B is the area of interest. Alternatively, the extent of a substantially laterally extensible area and/or the presence of a high modulus region may be apparent upon visual inspection of the article or may be suspected based on other facts. Where the extent of the area and/or the presence of the region is uncertain, the area of interest can be determined by testing various portions of one or more samples of a disposable wearable absorbent article with the steps of the modulus mapping method, as will be understood by one of ordinary skill in the art.

A second step in the modulus mapping method is to cut the area of interest from the disposable wearable absorbent article. If the area of interest is a side panel of a disposable wearable absorbent article, then continuous cuts are made through the article along one or more paths between the side panel and the rest of the article. Any connections in the side panel are left fastened and/or intact, so the area of interest can be a continuous portion of the article. If the area of interest is a side ear of a refastenable disposable wearable absorbent article, then continuous cuts are made through the article along one or more paths between the side ear and the rest of the article. If the side ear is fastened, then it is unfastened, for complete removal from the article. FIG. 8C illustrates an enlarged view of the extensible side ear 820B of the disposable wearable absorbent article 800B of the embodiment of FIG. 8B, unfastened and cut from the article 800B for testing with the modulus mapping method. For other areas of interest, including areas that are more than or less than a side panel or a side ear, continuous cuts are made through the article, on both sides of the area, from points on a waist edge of the article, cutting on paths perpendicular to the waist edge. These cuts either continue until they reach a leg opening of the article, or turn to reach the leg opening on the shortest cutting path parallel to the waist edge. Any connections in the area of interest are left fastened and/or intact, so the area of interest can be a continuous portion of the article.

A third step in the modulus mapping method is to mark the area of interest with a map, which is a grid of squares. While the area of interest is marked, the area is laid out flat, so the surface of the area of interest is not disturbed or distorted. In general, the gridlines of the map should run parallel to and perpendicular to the lateral direction of the disposable wearable absorbent article. However, if the material of the area of interest has a primary direction of elasticity, stretchability, or extensibility, then the gridlines of the map should run parallel to and perpendicular to that primary direction of stretch. Each of the squares in the grid is 5.0 millimeters by 5.0 millimeters. The gridlines can be measured in various ways, such as by using a calibrated ruler. The gridlines can also be marked in various ways, such as by using a fine tipped marking pen. The marked map is a grid of squares with rows R1 through Rn and columns C1 through Cn. Thus, each square on the map can be uniquely referenced by row and column number (e.g. C1:R1 for the square of column 1, row 1).

FIG. 8C illustrates an enlarged view of the extensible side ear 820B of the disposable wearable absorbent article 800B of the embodiment of FIG. 8B, unfastened and cut from the article 800B and marked with a map 8172, for testing with the modulus mapping method. FIG. 8B illustrates directions of laterally inboard and laterally outboard (using the lateral directions for the back 840 for ease of reference) as well as directions for longitudinally inboard and longitudinally outboard. The extensible side ear 820B also includes a longitudinally outboard side edge 825, a laterally inboard side edge 845, a laterally outboard side edge 865, and a longitudinally inboard side edge 885. In the embodiment of FIG. 8C, the material of the area of interest has a primary direction of stretchability in the lateral direction. Therefore, the map 8172 is marked on the extensible side ear 820B, as described above, so that the gridlines of the map 8172 run parallel to and perpendicular to that primary direction of stretch, which is the lateral direction.

A fourth step in the modulus mapping method is to test the area of interest. The dimensions of the area of interest are measured and recorded, for use in calculating modulus of elasticity. To determine thickness of material, a 3.14 cm2 round foot caliper is used, with 0.5 kPa of pressure and 10 seconds of residence time.

The testing uses a constant rate of extension tensile tester, fitted with a 5 N load cell. The tensile tester includes a computer interface, such as a MTS Alliance with TestWorks 4 software (available from MTS Systems Corp., Eden Prairie, Minn.). With regard to the test equipment described below, dimensions are given as precise values. The tensile tester is fitted with a set of 10 N Advantage™ pneumatic grips (available from MTS as part 100-032-017) and 15 millimeter wide by 8 millimeter high 10 N Advantage™ grip faces with smooth steel surface (available from MTS as part 56-163-702). Each of the grip faces is modified by mounting a hard rubber facing on the grip face. The rubber facing is a hard neoprene rubber with a Durometer rating of 70 A. The rubber facing is 5.00 millimeters wide by 8.0 millimeters high by 2.0 millimeters deep. The rubber facing is centered on the base width of the grip face. When the pneumatic grips are closed, the rubber facings should be vertically and horizontally aligned.

FIG. 8D illustrates a modified pneumatic grip 8101, as described above, for use in the modulus mapping method. The modified pneumatic grip 8101 includes base grip width 8102 (15 millimeters) and base grip height 8103 (8 millimeters). The modified pneumatic grip 8101 also includes a hard rubber facing 8105 with a facing width 8106 (5.00 millimeters), a facing height 8107 (8.0 millimeters), and a facing depth 8108 (2.0 millimeters).

Using this test equipment, the area of interest is tested with the modulus mapping method as follows. For clarity, in this description of testing, references to the area of interest refer to the extensible side ear 820B of the embodiment of FIG. 8C. The data acquisition rate of the tensile tester is set to 100 Hz and the gage length is set to 5.0 mm. The crosshead and the load cell are zeroed.

If there is no primary direction of elasticity, stretchability, or extensibility in the area of interest, then the area of interest is inserted and aligned as described below. The area of interest is inserted into the upper pneumatic grip at the square C1:R1 and oriented to pull the extensible side ear 820B in the lateral direction of the disposable wearable absorbent article. The upper grip is aligned outside of square C1:R1, along the laterally outboard gridline of the square C1:R1, and closed. The area of interest is also inserted into the lower pneumatic grip, aligned outside of square C1:R1, along the laterally inboard gridline of the square, and closed.

If there is a primary direction of elasticity, stretchability, or extensibility in the area of interest, then the area of interest is inserted and aligned as described below. The area of interest is inserted into the upper pneumatic grip at the square C1:R1 and oriented to pull the extensible side ear 820B in the primary direction of stretch. The upper grip is aligned outside of square C1:R1, along a first gridline of the square that is perpendicular to the primary direction of stretch, and closed. The area of interest is also inserted into the lower pneumatic grip, aligned outside of square C1:R1, along a second gridline of the square that is opposite from the first gridline and also perpendicular to the primary direction of stretch, and closed.

The area of interest should be under enough tension to eliminate any slack, but with less than 0.02 N of force on the load cell. The tensile tester is started and data is collected. The grips are moved apart at a constant rate of 25 millimeters per minute to 10% strain. The modulus of elasticity of the square is calculated as a directional modulus of elasticity, since the area of interest is pulled in a particular direction, e.g. the lateral direction or the primary direction of stretch. The directional modulus of elasticity of the square is calculated as the slope of the linear region of the resulting stress versus strain curve, using a slope segment length of 50% to determine the modulus line.

Figure 8E:
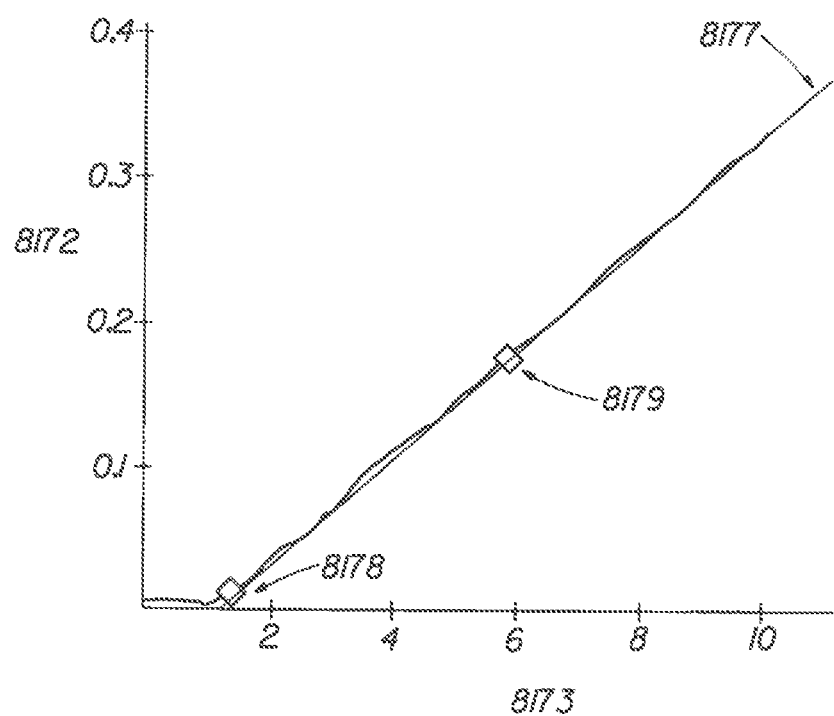
FIG. 8E illustrates an exemplary graph of the modulus of elasticity of a square of the map of the embodiment of FIG. 8C, according to embodiments of the present disclosure.

As an example, FIG. 8E illustrates an exemplary graph of the modulus of elasticity of a square of the map 8172, with stress 8172 in mega Pascals versus strain 8173 as a percentage, and a modulus line 8177 using a slope segment length of 50% from point 8178 to point 8179. The directional modulus of elasticity is determined to ±0.01 mega Pascals and recorded. This testing procedure is repeated for each square on the map, testing the first column (from C1:R1 to C1:Rn) followed by each successive column (from C2 to Cn). FIG. 8F illustrates an exemplary chart with directional modulus of elasticity values in mega Pascals, obtained from the modulus mapping method testing and recorded for each square of the map 8172 of the area of interest, which is the extensible side ear 820B.

A fifth step in the modulus mapping method is to plot and evaluate the directional modulus of elasticity values obtained from the modulus mapping method testing. The directional modulus of elasticity values are transferred to a spreadsheet such as Microsoft Excel™ and plotted as a surface contour plot. For the plot, set the maximum Z-axis value to truncate high modulus values resulting from margins, seams, chassis bonds, and/or other such structural discontinuities in the area of interest that are unrelated to the substantially laterally extensible area or the high modulus region. As an example, a maximum value of approximately six times the upper value of the directional modulus of elasticity in the lowest modulus region is useful for the directional modulus of elasticity values in the embodiment of FIG. 8F. Choose major value intervals to visually evaluate the plot for existing patterns of high directional modulii of elasticity in the area of interest. A minimum of five intervals should be used for this evaluation. For example, an interval value of approximately 0.25 mega Pascals is useful for the directional modulus of elasticity values in the embodiment of FIG. 8F. One skilled in the art of visual pattern recognition will understand that these values are representative and can be determined empirically for a given set of directional modulus of elasticity values.

Figure 8G:
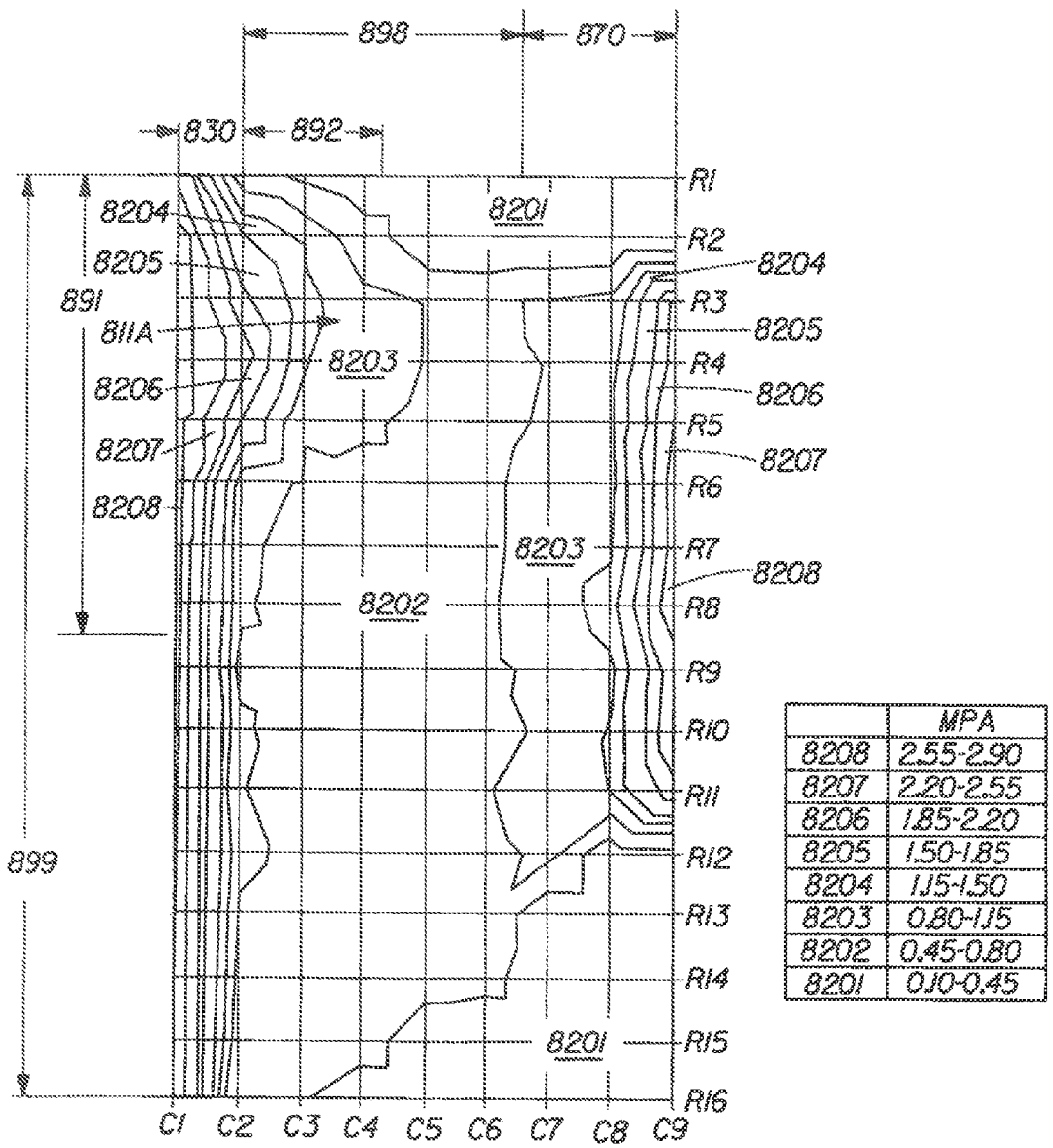
FIG. 8G illustrates an exemplary surface contour plot of the modulus of elasticity values of the chart of the embodiment of FIG. 8F, according to embodiments of the present disclosure.

FIG. 8G illustrates an exemplary surface contour plot of the directional modulus of elasticity values of the chart of the embodiment of FIG. 8F, as described above, for use in the modulus mapping method. In FIG. 8G, the maximum Z-axis values are truncated at 2.90 mega Pascals, which is about six times the upper value of the directional modulus of elasticity in the lowest modulus region (e.g. 0.45 mega Pascals). The major value intervals are chosen to be 0.35 mega Pascals. One skilled in the art of visual pattern recognition will recognize that the plot of FIG. 8G illustrates the presence of a high modulus region 811B within a first area of a substantially laterally extensible area, similar to the embodiment of FIG. 8A. Further, the plot of FIG. 8G indicates that the high modulus region 811B has a directional modulus of elasticity between 0.80 and 1.15 mega Pascals while substantially all of the portion of the substantially laterally extensible area that is outside of the high modulus region 811B has a directional modulus of elasticity between about 0.45 and 0.80 mega Pascals. Thus, the modulus mapping method can be used to determine the extent of a substantially laterally extensible area and to detect the presence of a high modulus region within an extensible side, as well as to measure particular directional modulus of elasticity values for the area and the region.

The modulus mapping method can be used to determine the locations, dimensions, and directional modulus of elasticity values for a first area, a second area, a third area, and a fourth area of the substantially laterally extensible area. Such dimensions can be measured by using the known scale of the map of gridlines for the portion of the map that is of interest. The modulus mapping method can also be used to determine values for a widest lateral dimension and a longest longitudinal dimension of a high modulus region, as well as for a high modulus region lateral offset and a high modulus region longitudinal offset. The modulus mapping method can further be used to determine other relevant locations, dimensions, and directional modulus of elasticity values, as will be understood by one of ordinary skill in the art.

Figure 8H:
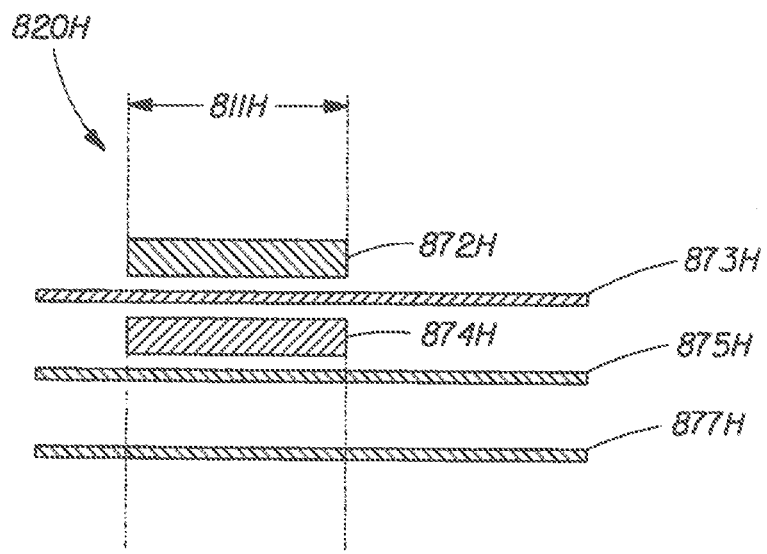
FIG. 8H illustrates a side view of an embodiment of a high modulus region in a first area of a substantially laterally extensible area of an extensible side of a disposable wearable absorbent article according to embodiments of the present disclosure.

FIG. 8H illustrates a side view of an embodiment of a high modulus region 811H in a first area of a substantially laterally extensible area of an extensible side 820H of a disposable wearable absorbent article according to embodiments of the present disclosure. The substantially laterally extensible area is a laminate material, including a first nonwoven layer 873H joined to an elastic layer 875H, which is joined to a second nonwoven layer 877H. The high modulus region 811H is formed on a portion of the substantially laterally extensible area by using of a first bonding agent 872H provided externally to a surface of the first nonwoven layer 873H and a second bonding agent 874H provided internally between the first nonwoven layer 873H and the elastic layer 875H. In various embodiments, either or both of the bonding agents can be adhesives, polymers, other materials, or combinations of these, provided as described in connection with the embodiment of FIG. 8A. In various embodiments, either the first bonding agent 872H or the second bonding agent 874H can be used independently to form the high modulus region 811H. In some embodiments, a bonding agent can additionally or alternatively be similarly provided on one or more other surfaces or between one or more other layers of the substantially laterally extensible area, as will be understood by one of ordinary skill in the art.

Figure 8I:
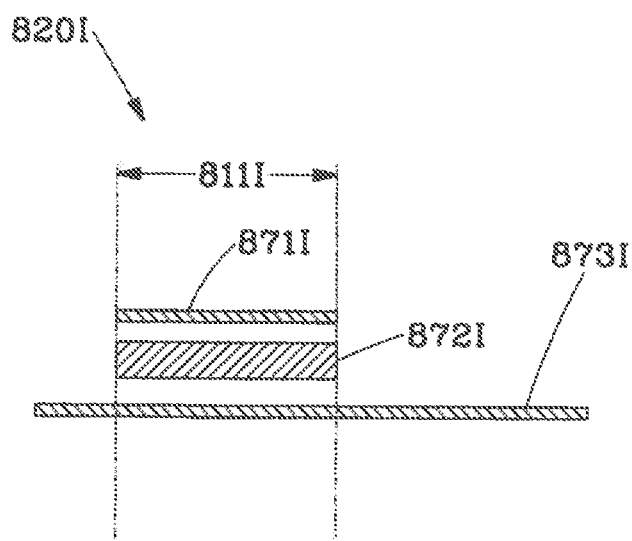
FIG. 8I illustrates a side view of an additional embodiment of a high modulus region in a first area of a substantially laterally extensible area of an extensible side of a disposable wearable absorbent article according to embodiments of the present disclosure.

FIG. 8I illustrates a side view of an additional embodiment of a high modulus region in a first area of a substantially laterally extensible area of an extensible side 820I of a disposable wearable absorbent article according to embodiments of the present disclosure. The substantially laterally extensible area includes a first layer 873I. The high modulus region 811I is formed on a portion of the substantially laterally extensible area by joining an additional material 871I by using a first bonding agent 872I provided externally to a surface of the first layer 873I. In various embodiments, the additional material 871I can be joined to the substantially laterally extensible area without using a bonding agent, provided as described in connection with the embodiment of FIG. 8A. In some embodiments, a bonding agent can additionally or alternatively be similarly provided on one or more other surfaces or between one or more other layers of the substantially laterally extensible area, as will be understood by one of ordinary skill in the art.

Figure 9A:
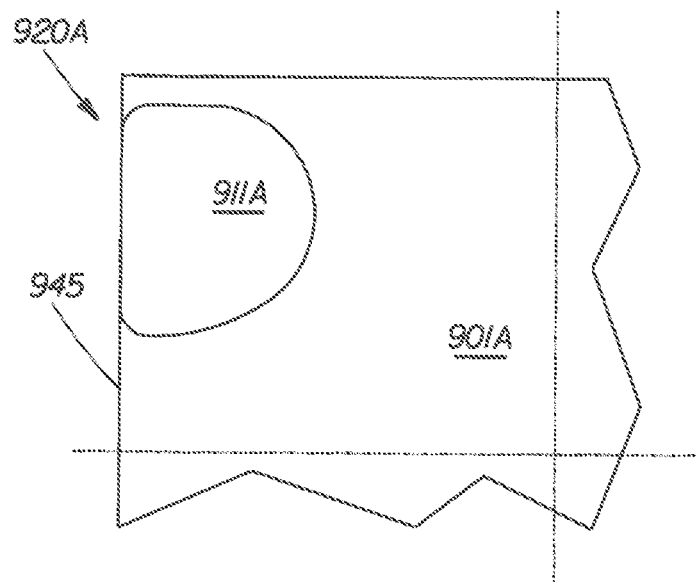
FIG. 9A illustrates a top view of an additional embodiment of a high modulus region in a first area of a substantially laterally extensible area of an extensible side of a disposable wearable absorbent article according to embodiments of the present disclosure.
Figure 9B:
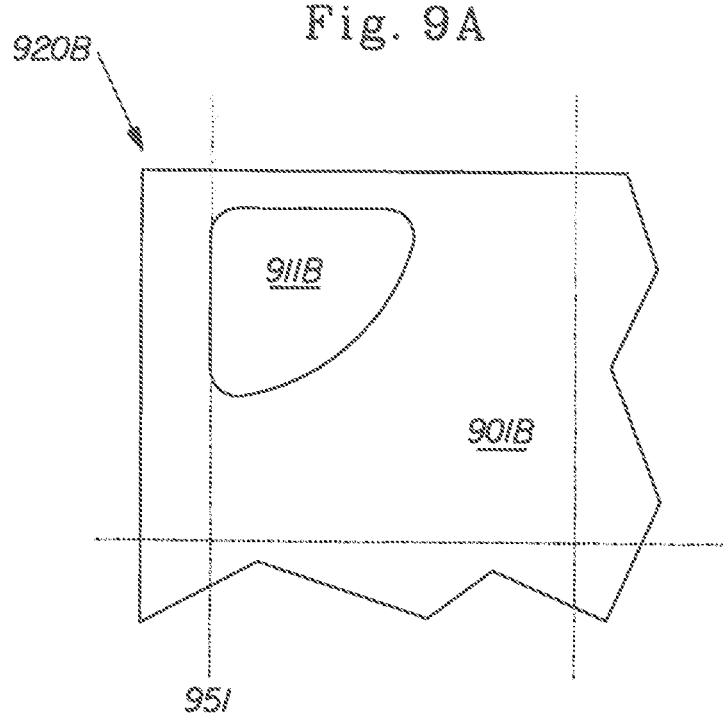
FIG. 9B illustrates a top view of a further embodiment of a high modulus region in a first area of a substantially laterally extensible area of an extensible side of a disposable wearable absorbent article according to embodiments of the present disclosure.

FIGS. 9A and 9B illustrate various locations for a high modulus region in a first area of a substantially laterally extensible area of an extensible side of a disposable wearable absorbent article according to embodiments of the present disclosure. In various embodiments, each of extensible sides 920A and 920B of the embodiments of FIGS. 9A and 9B can be the extensible side 820A of the embodiment of FIG. 8A and one or more of the elements of the embodiments of FIGS. 9A and 9B can be the like-numbered element of the embodiment of FIG. 8A.

FIG. 9A illustrates a top view of an additional embodiment of a high modulus region 911A in a first area 901A of a substantially laterally extensible area of an extensible side 920A of a disposable wearable absorbent article according to embodiments of the present disclosure. In FIG. 9A, the extensible side 920A is illustrated in part. The high modulus region 911A is bounded by a region boundary with an overall half circle shape. The region boundary partially coincides with a laterally inboard side edge 945 of the extensible side 920A.

FIG. 9B illustrates a top view of a further embodiment of a high modulus region 911B in a first area 901B of a substantially laterally extensible area of an extensible side 920B of a disposable wearable absorbent article according to embodiments of the present disclosure. In FIG. 9B, the extensible side 920B is illustrated in part. The high modulus region 911B is bounded by a region boundary with an overall quarter circle shape. The region boundary partially coincides with a first lateral reference line 951.

FIGS. 10A-12 illustrate various configurations of a high modulus region in a first area of a substantially laterally extensible area of an extensible side of a disposable wearable absorbent article according to embodiments of the present disclosure. In some embodiments, the substantially laterally extensible areas of FIGS. 10A-12 can include a zero-strain laminate. In various embodiments, each of extensible sides 1020A, 1020B, 1020C, 1120A, 1120B, 1120C, and 1220 of the embodiments of FIGS. 10A-12 can be the extensible side 820A of the embodiment of FIG. 8A and one or more of the elements of the embodiments of FIGS. 10A-12 can be the like-numbered element of the embodiment of FIG. 8A.

Figure 10A:
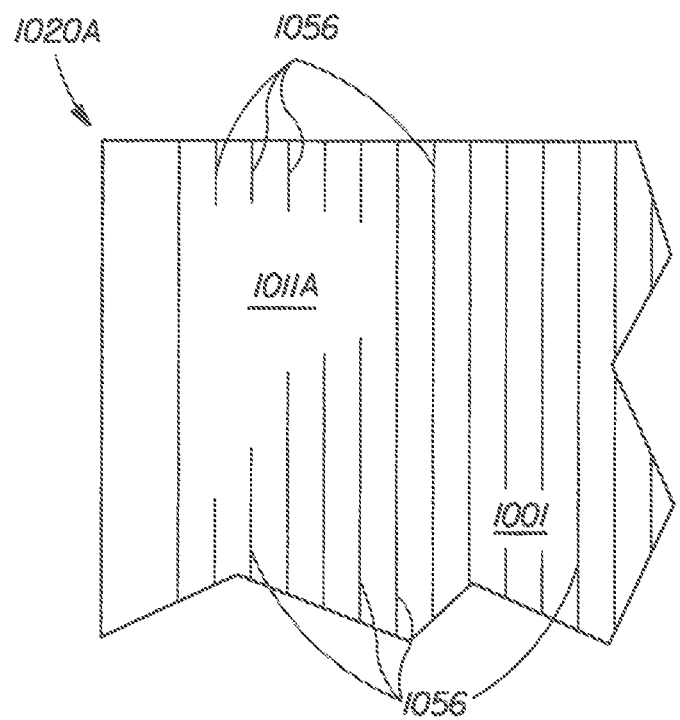
FIG. 10A illustrates a top view of an embodiment of an unactivated high modulus region in a first area of an activated substantially laterally extensible area of an extensible side of a disposable wearable absorbent article according to embodiments of the present disclosure.

FIG. 10A illustrates a top view of an embodiment of an unactivated high modulus region 1011A in a first area 1001 of an activated substantially laterally extensible area of an extensible side 1020A of a disposable wearable absorbent article according to embodiments of the present disclosure. In FIG. 10A, the extensible side 1020A is illustrated in part. In the embodiment of FIG. 10A, substantially all of the unactivated high modulus region 1011A is not mechanically activated, as indicated by the absence of mechanical activation lines. Substantially all of the substantially laterally extensible area that is outside of the unactivated high modulus region 1011A is mechanically activated, as indicated by mechanical activation lines 1056.

Figure 10B:
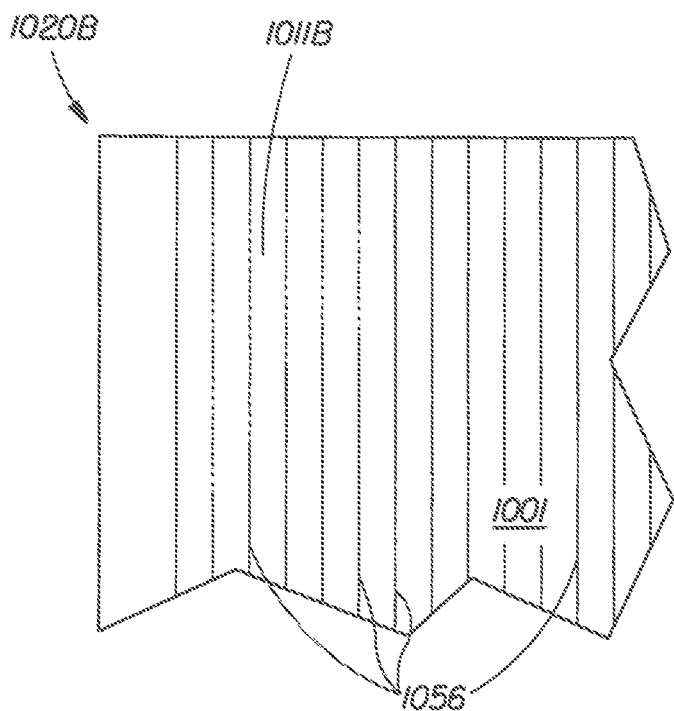
FIG. 10B illustrates a top view of an embodiment of a partially mechanically activated high modulus region in a first area of an activated substantially laterally extensible area of an extensible side of a disposable wearable absorbent article according to embodiments of the present disclosure.

FIG. 10B illustrates a top view of an embodiment of a partially mechanically activated high modulus region 1011B in a first area 1001 of an activated substantially laterally extensible area of an extensible side 1020B of a disposable wearable absorbent article according to embodiments of the present disclosure. In FIG. 10B, the extensible side 1020B is illustrated in part. In the embodiment of FIG. 10B, substantially all of the partially mechanically activated high modulus region 1011B is partially mechanically activated with a first particular level of pre-strain, as indicated by broken portions of mechanical activation lines 1056 in the partially mechanically activated high modulus region 1011B. Substantially all of the substantially laterally extensible area that is outside of the partially mechanically activated high modulus region 1011B is mechanically activated with a level of pre-strain that is greater than the first particular level of pre-strain, as indicated by solid portions of the mechanical activation lines 1056 in the first area 1001.

Figure 10C:
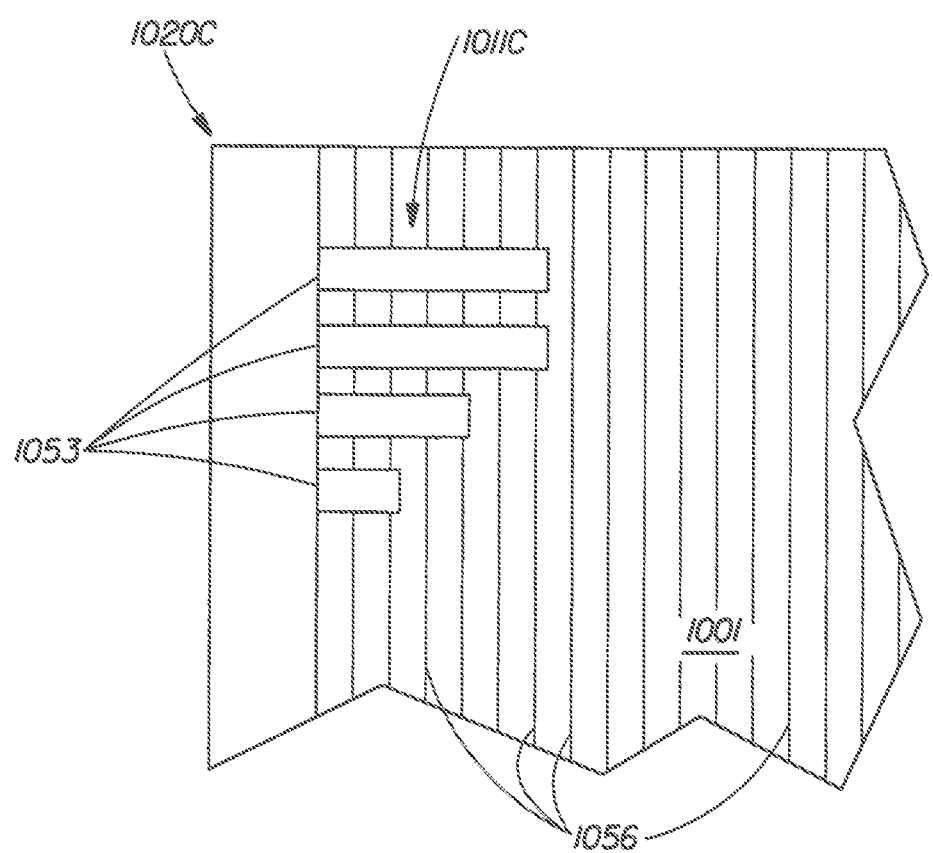
FIG. 10C illustrates a top view of an embodiment of a SELF activated high modulus region in a first area of an activated substantially laterally extensible area of an extensible side of a disposable wearable absorbent article according to embodiments of the present disclosure.

FIG. 10C illustrates a top view of an embodiment of a SELF activated high modulus region 1011C in a first area 1001 of an activated substantially laterally extensible area of an extensible side 1020C of a disposable wearable absorbent article according to embodiments of the present disclosure. In FIG. 10C, the extensible side 1020C is illustrated in part. In the embodiment of FIG. 10C, substantially all of the SELF activated high modulus region 1011C is SELF activated with a first particular level of pre-strain, as indicated by unactivated lateral bands 1053 in the SELF activated high modulus region 1011C. The level of pre-strain, along with the size and shape of the unactivated lateral bands 1053 can be configured in a number of ways to provide for various lateral extensibilities in the SELF activated high modulus region 1011C. Substantially all of the substantially laterally extensible area that is outside of the SELF activated high modulus region 1011C is mechanically activated with a second particular level of pre-strain, as indicated by mechanical activation lines 1056 in the first area 1001. In various embodiments, the second particular level of pre-strain may be the same as, less than, or greater than the first particular level of pre-strain.

Figure 11A:
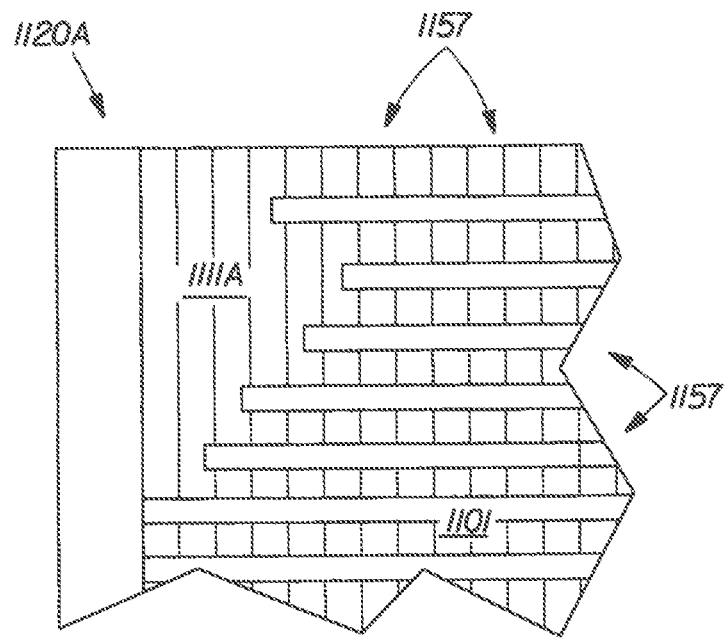
FIG. 11A illustrates a top view of an embodiment of an unactivated high modulus region in a first area of a SELF activated substantially laterally extensible area of an extensible side of a disposable wearable absorbent article according to embodiments of the present disclosure.

FIG. 11A illustrates a top view of an embodiment of an unactivated high modulus region 1111A in a first area 1101 of a SELF activated substantially laterally extensible area of an extensible side 1120A of a disposable wearable absorbent article according to embodiments of the present disclosure. In FIG. 11A, the extensible side 1120A is illustrated in part. In the embodiment of FIG. 11A, substantially all of the unactivated high modulus region 1111A is not mechanically activated, as indicated by the absence of mechanical activation lines. Substantially all of the substantially laterally extensible area that is outside of the unactivated high modulus region 1111A is SELF activated 1157, as indicated by mechanical activation lines and unactivated lateral bands in the first area 1101.

Figure 11B:
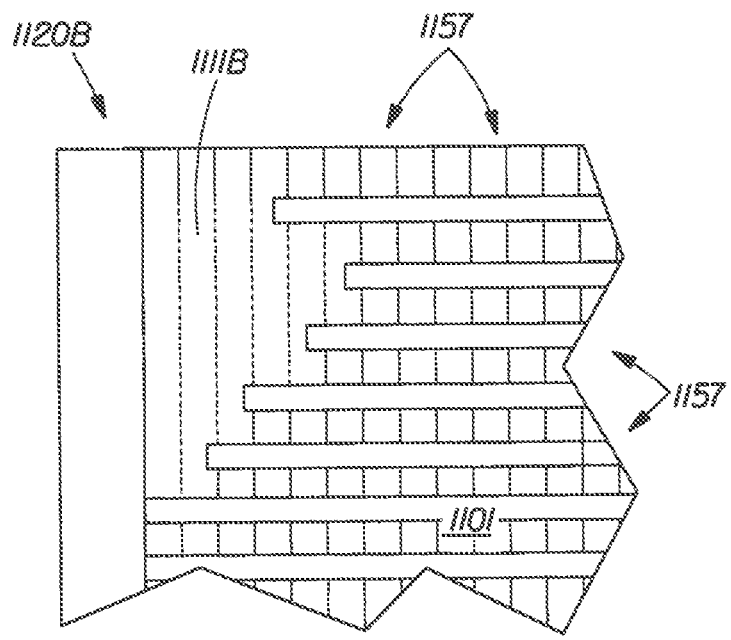
FIG. 11B illustrates a top view of an embodiment of a partially mechanically activated high modulus region in a first area of a SELF activated substantially laterally extensible area of an extensible side of a disposable wearable absorbent article according to embodiments of the present disclosure.

FIG. 11B illustrates a top view of an embodiment of a partially mechanically activated high modulus region 1111B in a first area 1101 of a SELF activated substantially laterally extensible area of an extensible side 1120B of a disposable wearable absorbent article according to embodiments of the present disclosure. In FIG. 11B, the extensible side 1120B is illustrated in part. In the embodiment of FIG. 11B, substantially all of the partially mechanically activated high modulus region 1111B is partially mechanically activated, as indicated by broken portions of mechanical activation lines in the partially mechanically activated high modulus region 1111B. The partially mechanically activated high modulus region 1111B can be configured with various levels of pre-strain to provide for various lateral extensibilities. Substantially all of the substantially laterally extensible area that is outside of the unactivated high modulus region 1111A is SELF activated 1157, as indicated by mechanical activation lines and unactivated lateral bands in the first area 1101.

Figure 11C:
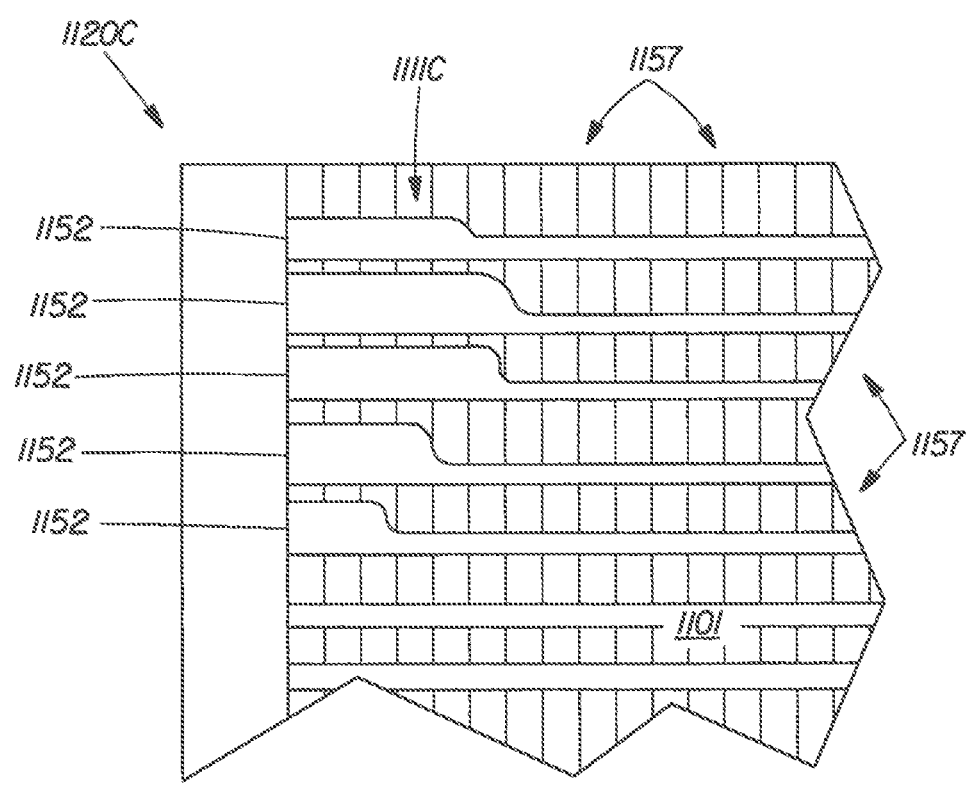
FIG. 11C illustrates a top view of an embodiment of a SELF activated high modulus region in a first area of a SELF activated substantially laterally extensible area of an extensible side of a disposable wearable absorbent article according to embodiments of the present disclosure.

FIG. 11C illustrates a top view of an embodiment of a SELF activated high modulus region 1111C in a first area 1101 of a SELF activated substantially laterally extensible area of an extensible side 1120C of a disposable wearable absorbent article according to embodiments of the present disclosure. In FIG. 11C, the extensible side 1120C is illustrated in part. In the embodiment of FIG. 11C, substantially all of the SELF activated high modulus region 1111C is SELF activated with a first particular level of pre-strain, as indicated by unactivated lateral bands 1152 in the SELF activated high modulus region 1111C. The level of pre-strain, along with the size and shape of the unactivated lateral bands 1153 can be configured in a number of ways to provide for various lateral extensibilities in the SELF activated high modulus region 1111C. Substantially all of the substantially laterally extensible area that is outside of the SELF activated high modulus region 1111C is SELF activated 1157 with a second particular level of pre-strain, as indicated by mechanical activation lines and unactivated lateral bands in the first area 1101 that are narrower than the unactivated lateral bands 1153. In various embodiments, the second particular level of pre-strain may be the same as, less than, or greater than the first particular level of pre-strain.

Figure 12:
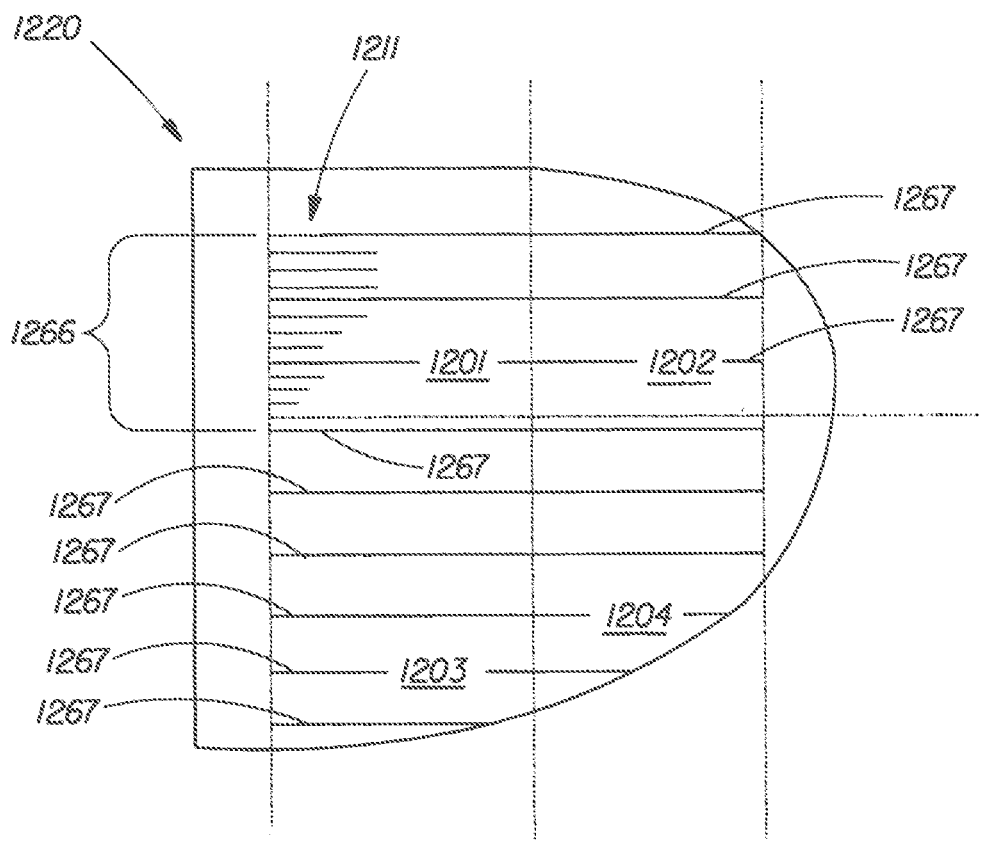
FIG. 12 illustrates a top view of a still further embodiment of a high modulus region in a first area of a substantially laterally extensible area of an extensible side of a disposable wearable absorbent article according to embodiments of the present disclosure.

FIG. 12 illustrates a top view of a still further embodiment of a high modulus region 1211 in a first area 1201 of a substantially laterally extensible area of an extensible side 1220 of a disposable wearable absorbent article according to embodiments of the present disclosure. The substantially laterally extensible area includes the first area 1201, a second area 1202, a third area 1203, and a fourth area 1204. The substantially laterally extensible area includes first elastic strands 1267 extending laterally across the area. The high modulus region 1211 includes second elastic strands 1266 in addition to the first elastic strands 1267. In some embodiments, the second elastic strands 1266 are configured to be disposed only in the high modulus region 1211 and/or portions of the second elastic strands that extend beyond the high modulus region 1211 can be rendered ineffective.

FIGS. 13A through 16B illustrate various embodiments of disposable wearable absorbent articles with extensible sides including substantially laterally extensible areas. While not wishing to be bound by this theory, it is believed that, in each of the embodiments of FIGS. 13A through 16B, tensile forces can be directed through a first area of a substantially laterally extensible area to an upper portion of the article proximate to a waist edge of the article. Thus, disposable wearable absorbent articles of the present disclosure can provide extensible sides that extend easily and can help disposable wearable absorbent articles to fit snugly, stay in place, and not leak. FIGS. 13A, 13B and 15A through 18 illustrate various embodiments of for disposable wearable absorbent articles with extensible side ears. These embodiments can also be adapted for use as disposable wearable absorbent articles with extensible side panels, as will be understood by one of ordinary skill in the art. In the embodiments of FIGS. 13A through 16B relative directions for laterally inboard, laterally outboard, longitudinally outboard, and longitudinally inboard, with respect to a disposable wearable absorbent article, are used as described in connection with the embodiments of FIGS. 5, 6, and 8A.

Figure 13A:
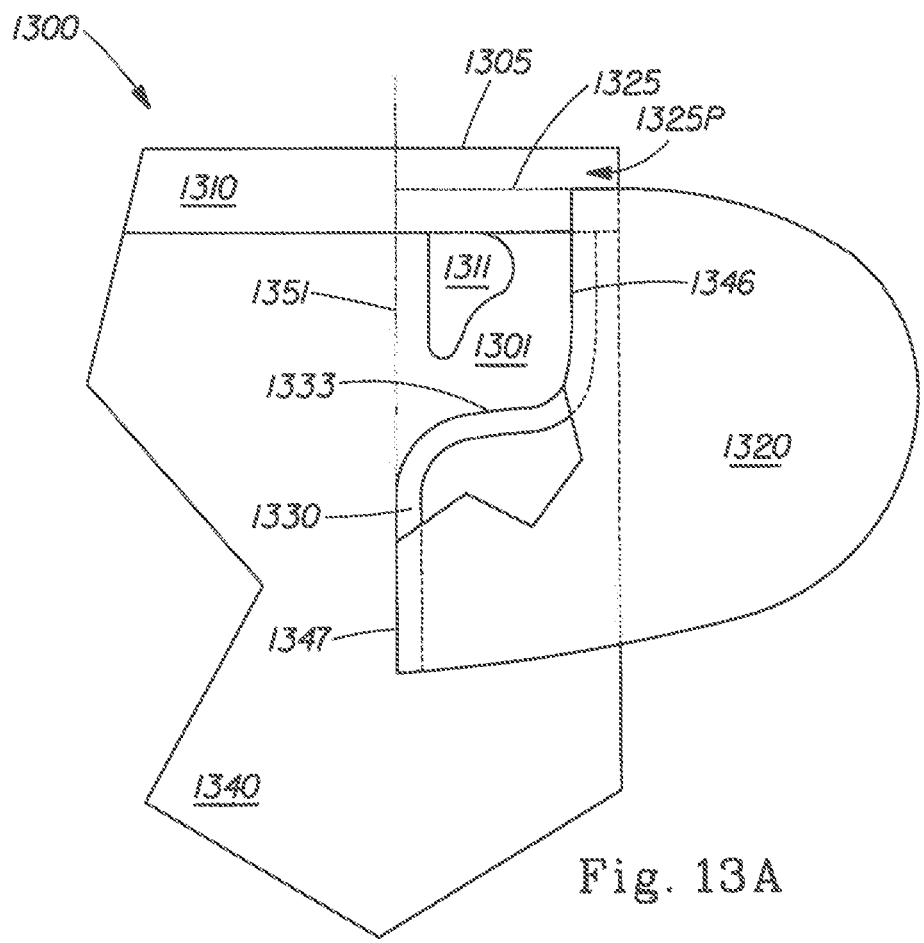
FIG. 13A illustrates a top view of an embodiment of a portion of a disposable wearable absorbent article including an extensible side according to the present disclosure.

FIG. 13A illustrates a top view of an embodiment of a portion of a disposable wearable absorbent article 1300 including an extensible side 1320 according to the present disclosure. In FIG. 13A, the disposable wearable absorbent article 1300 is illustrated in part. The extensible side 1320 is a side ear and is connected to a back 1340 of the disposable wearable absorbent article by a side connection 1330, which is illustrated in a cut-away portion of the extensible side 1320. The side connection 1330 includes a longitudinal portion of the side connection 1333. The extensible side 1320 includes a furthest longitudinally outboard point 1325P, a longitudinally outboard portion of a laterally inboard side edge 1346, and a longitudinally inboard portion of a laterally inboard side edge 1347. FIG. 13A also illustrates a first area 1301 with a high modulus region 1311, a back waist edge 1305, and a back upper portion 1310 of the disposable wearable absorbent article 1300. The embodiment of FIG. 13A also includes a first area longitudinally outboard boundary portion 1325 and a first lateral reference line 1351. The disposable wearable absorbent article 1300 of the embodiment of FIG. 13A can be configured to be worn by a wearer such that part or all of the first area 1301 is disposed above a PHIP of the wearer, as illustrated in FIGS. 17A and 17B. In some embodiments, the disposable wearable absorbent article 1300 of the embodiment of FIG. 13A can be configured to be worn by a wearer such that part or all of the first area 1301 and/or part or all of the high modulus region 1311 is disposed above a PHIP of the wearer, as illustrated in FIGS. 17A and 17B.

In the embodiment of FIG. 13A, the first area 1301 is a portion of a chassis of the disposable wearable absorbent article 1300. The first area 1301 is bounded by the first area longitudinally outboard boundary portion 1325, the longitudinal portion of the side connection 1333, the laterally inboard side edge 1346, and the first lateral reference line 1351. In the embodiment of FIG. 13A, the first area longitudinally outboard boundary portion 1325 extends laterally from the furthest longitudinally outboard point 1325P to the first lateral reference line 1351. Also in the embodiment of FIG. 13A, the first lateral reference line 1351 extends longitudinally from the back upper portion 1310 to the laterally inboard side edge 1346. In various embodiments, the extensible side 1320 can be the extensible side 820A of the embodiment of FIG. 8A and one or more of the elements of the embodiment of FIG. 13A can be the like-numbered element of the embodiment of FIG. 8A.

The extensible side 1320 includes a substantially laterally extensible area, adjacent to and substantially laterally outboard from the first area 1301 and adjacent to and substantially longitudinally inboard to the first area 1301. In various embodiments, the substantially laterally extensible area can be considered as including a second area, a third area, and a fourth area, as described in connection with the embodiment of FIG. 5. The extensible side 1320 also includes an overall lateral extensibility that is substantially greater than an overall lateral extensibility of the first area 1301. In the embodiment of FIG. 13A, the extensible side 1320 is connected to the back 1340, adjacent to the first area 1301, by using the side connection 1330.

In some embodiments, some or all of the side edges 1346 and 1347 can vary from the embodiment of FIG. 13A, in size, shape, alignment, and orientation. These edges can vary in size to accommodate extensible sides of various shapes and sizes. These side edges can take various shapes, such as straight lines, curves, irregularly shaped lines, angles, curves, and/or combinations of these. Such variations in the side edges can affect the size and/or shape of the first area 1301 in the fastening system 1300.

Figure 13B:
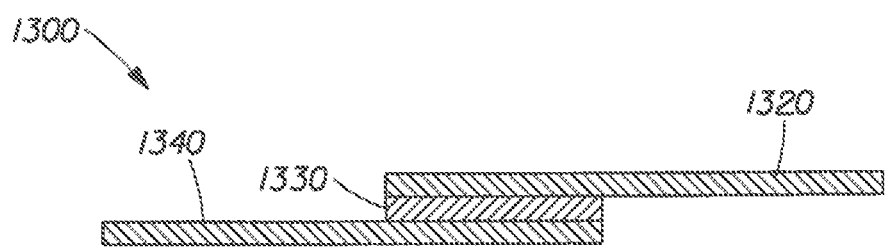
FIG. 13B illustrates a side view of the embodiment of FIG. 13A according to the present disclosure.

FIG. 13B illustrates a side view of the embodiment of FIG. 13A according to the present disclosure. The fastening system 1300 of FIG. 13B illustrates the extensible side 1320 connected to the back 1340 of the absorbent article by the connection 1330.

Figure 14:
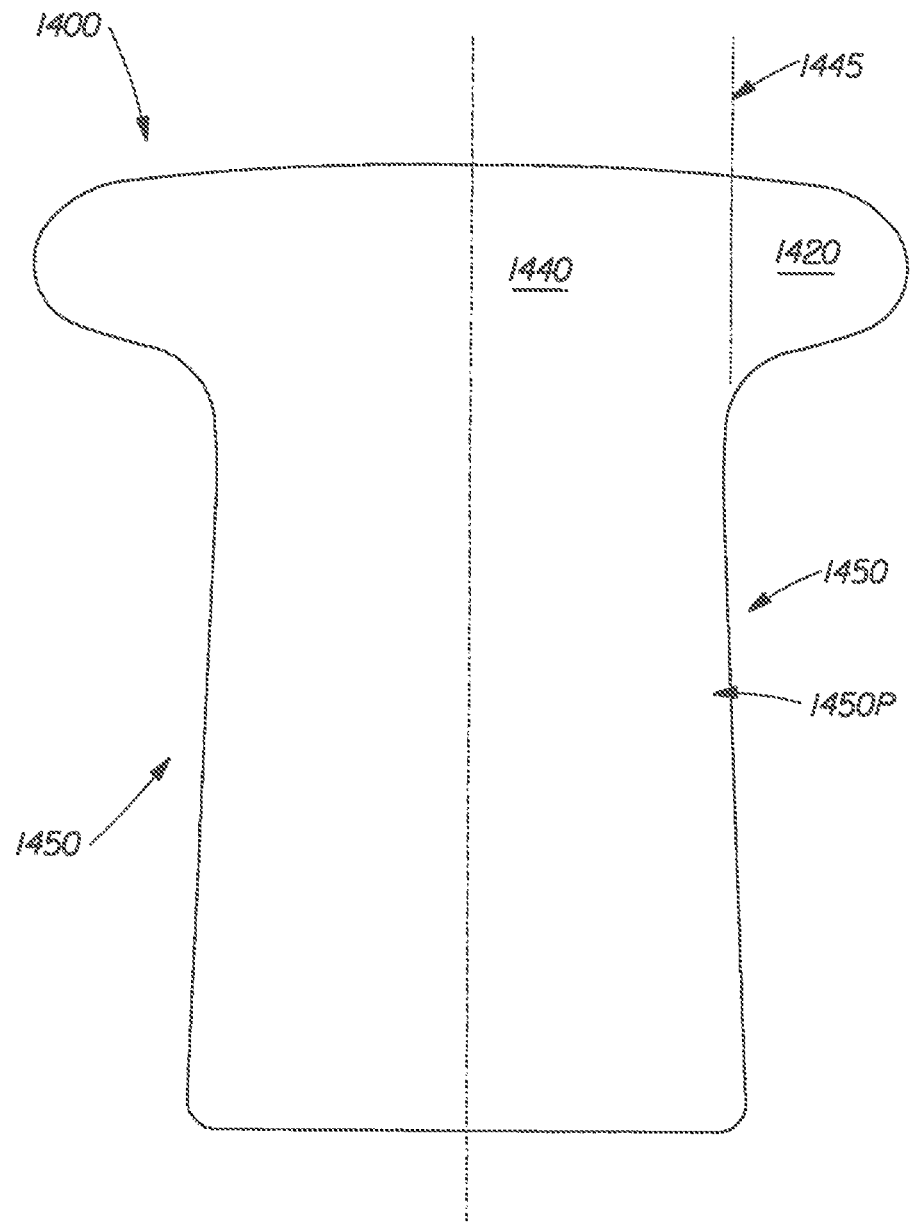
FIG. 14 illustrates a disposable wearable absorbent article with a unibody construction and an extensible side according to the present disclosure.

FIG. 14 illustrates a disposable wearable absorbent article 1400 with a unibody construction and an extensible side 1420 according to the present disclosure. The disposable wearable absorbent article includes a back 1440 and a crotch area 1450 with a furthest laterally inboard point 1450P. The extensible side 1420 is an extension of the back 1440 of the disposable wearable absorbent article 1400. FIG. 14 also includes a laterally inboard side edge 1445, which is considered as a straight line parallel to the lateral centerline, and coincident with the furthest laterally inboard point 1450P in the crotch area 1450 of the disposable wearable absorbent article 1400. In various embodiments, part or all of the back 1440 of the disposable wearable absorbent article can be laterally extensible and/or laterally inextensible. In some embodiments, in which the back 1440 and the extensible side 1420 are similarly substantially laterally extensible, a first lateral reference line can coincide with the laterally inboard side 1445, as described above.

Figure 15A:
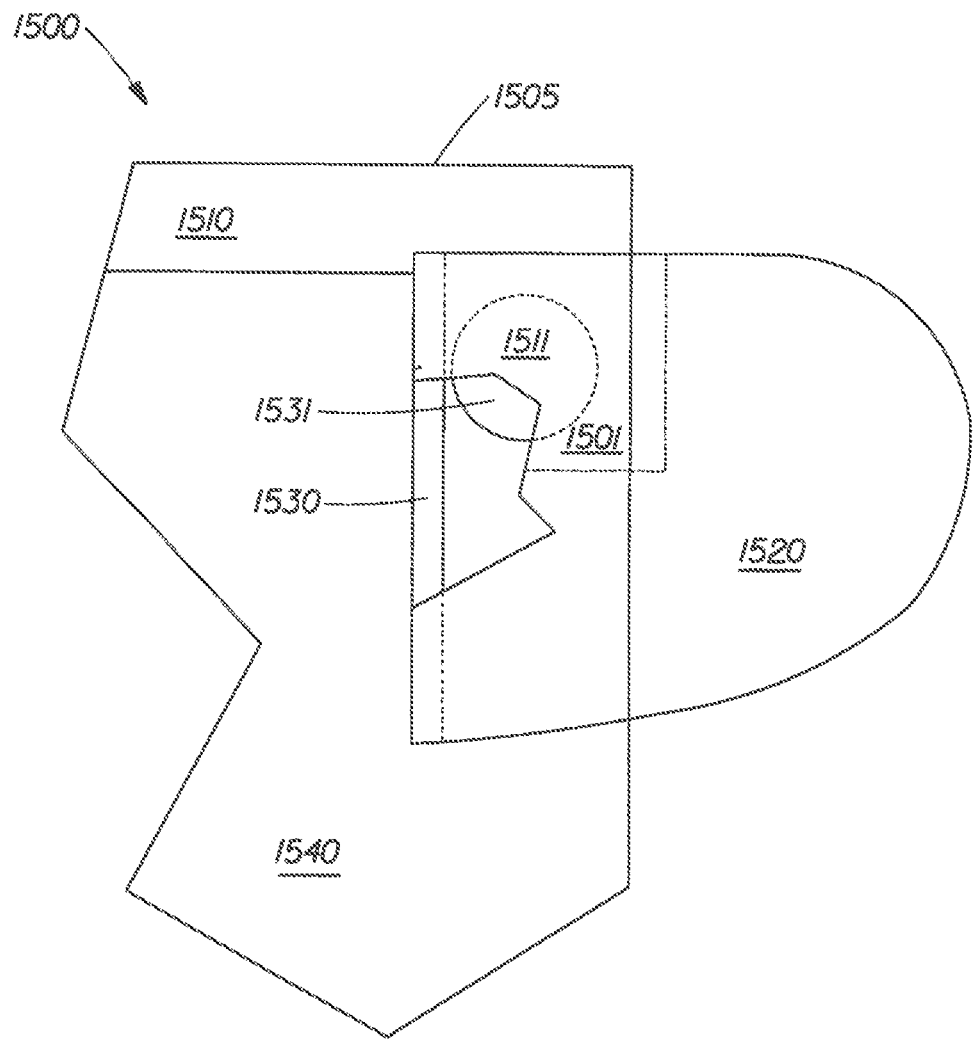
FIG. 15A illustrates a top view of an embodiment of a portion of a disposable wearable absorbent article including an extensible side with a subjacent connection according to the present disclosure.

FIG. 15A illustrates a top view of an embodiment of a portion of a disposable wearable absorbent article 1520 including an extensible side 1520 with a subjacent connection 1531 according to the present disclosure. In FIG. 15A, the disposable wearable absorbent article is illustrated in part. The extensible side 1520 is a side ear and is connected to a back 1540 of the disposable wearable absorbent article by a side connection 1530, along a laterally inboard side edge of the extensible side 1520. The side connection 1530 is illustrated in a cut-away portion of the extensible side 1520. The extensible side 1520 includes a first area 1501 with a region 1511, which is connected to the back 1540 with the subjacent connection 1531, which is disposed subjacent to the extensible side 1520. In various embodiments, the region 1511 can alternatively be connected to a layer of a disposable wearable absorbent article with a superjacent connection, disposed superjacent to the extensible side 1520. FIG. 15A also illustrates a back waist edge 1505, and a back upper portion 1510 of the disposable wearable absorbent article. The disposable wearable absorbent article of the embodiment of FIG. 15A can be configured to be worn by a wearer such that the first area 1501 is disposed above a posterior hip inflection protrusion of the wearer, as illustrated in FIGS. 17A and 17B

The extensible side 1520 includes a substantially laterally extensible area, adjacent to and substantially laterally outboard from the first area 1501, adjacent to and substantially longitudinally inboard to the first area 1501, and with an overall lateral extensibility that is substantially greater than an overall lateral extensibility of the first area 1501. In various embodiments, the extensible side 1520 can be the extensible side 820A of the embodiment of FIG. 8A and one or more of the elements of the embodiment of FIG. 15A can be the like-numbered element of the embodiment of FIG. 8A.

In various embodiments, the subjacent connection 1531 can be separate from or integral with the side connection 1530. The subjacent connection 1531 and/or the side connection 1530 can be any type of connection, such as a durable connection, a non-refastenable connector, a refastenable connector, adhesive, fusion bonds, etc.

Figure 15B:
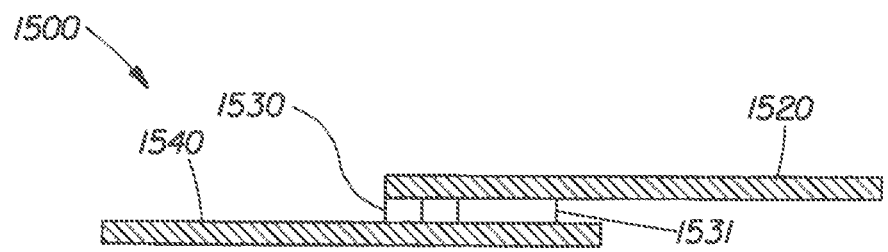
FIG. 15B illustrates a side view of the embodiment of FIG. 15A according to the present disclosure.

FIG. 15B illustrates a side view of the embodiment of FIG. 15A according to the present disclosure. The disposable wearable absorbent article 1520 of FIG. 15B illustrates the extensible side 1520 connected to back 1540 of the absorbent article by the connection 1530 and by the subjacent connection 1531.

Figure 16A:
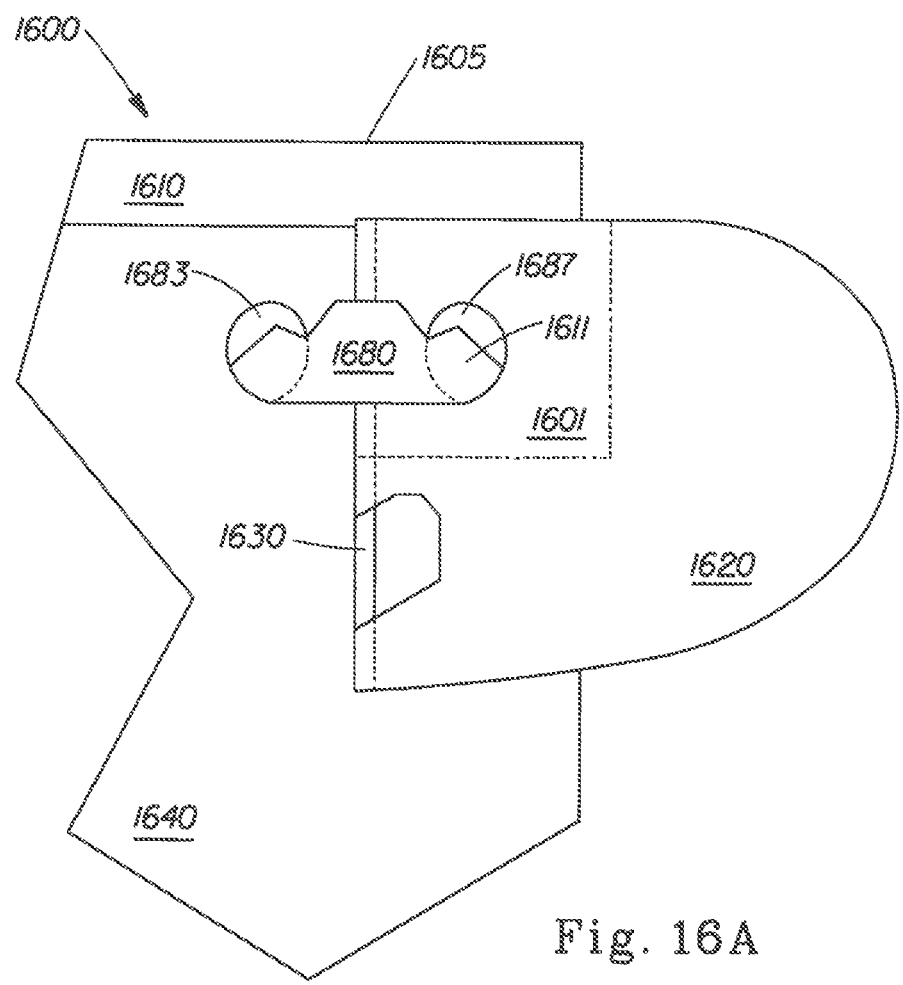
FIG. 16A illustrates a top view of an embodiment of a portion of a disposable wearable absorbent article with an extensible side and a regional connector according to the present disclosure.

FIG. 16A illustrates a top view of an embodiment of a portion of a disposable wearable absorbent article 1620 with an extensible side 1620 and a regional connector 1680 according to the present disclosure. In FIG. 16A, the disposable wearable absorbent article is illustrated in part. The extensible side 1620 is a side ear and is connected to a back 1640 of the disposable wearable absorbent article by a side connection 1630, along a laterally inboard side edge of the extensible side 1620. The side connection 1630 is illustrated in a cut-away portion of the extensible side 1620. The extensible side 1620 includes a first area 1601 with a region 1611. The regional connector 1680 includes a first end connected to the back 1640 with a first connection 1683 disposed laterally inboard to a laterally inboard side edge of the extensible side 1620. In alternate embodiments, the first connection 1683 can be disposed to at least partially coincide with the side connection 1630. The regional connector 1680 also includes a second end connected to the first area 1601 at the region 1611 with a second connection 1687. FIG. 16A also illustrates a back waist edge 1605, and a back upper portion 1610 of the disposable wearable absorbent article. The first connection 1683 and the second connection 1687 are illustrated in cut-away portions of the regional connector 1680. The disposable wearable absorbent article of the embodiment of FIG. 16A can be configured to be worn by a wearer such that the first area 1601 is disposed above a posterior hip inflection protrusion of the wearer, as illustrated in FIGS. 17A and 17B

The extensible side 1620 includes a substantially laterally extensible area, adjacent to and substantially laterally outboard from the first area 1601, adjacent to and substantially longitudinally inboard to the first area 1601, and with an overall lateral extensibility that is substantially greater than an overall lateral extensibility of the first area 1601. In various embodiments, the extensible side 1620 can be the extensible side 820A of the embodiment of FIG. 8A and one or more of the elements of the embodiment of FIG. 16A can be the like-numbered element of the embodiment of FIG. 8A.

Figure 16B:
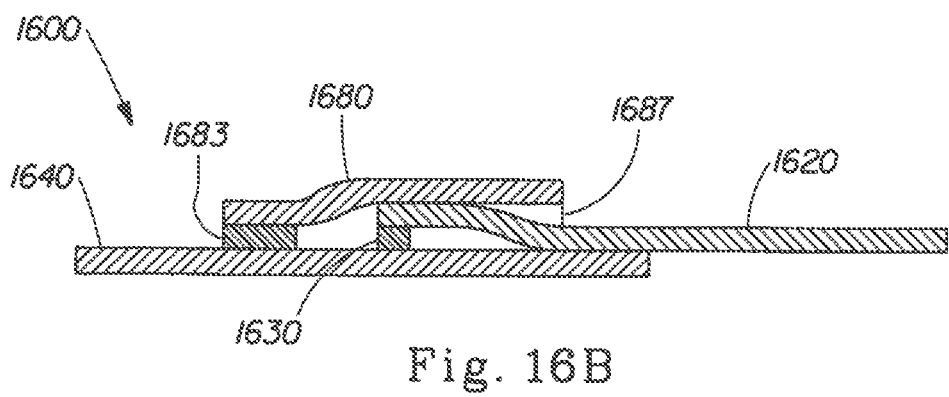
FIG. 16B illustrates a side view of the embodiment of FIG. 16A according to the present disclosure.

FIG. 16B illustrates a side view of the embodiment of FIG. 16A according to the present disclosure. The disposable wearable absorbent article 1620 of FIG. 16B illustrates the extensible side 1620 connected to back 1640 of the absorbent article by the connection 1630 and by the regional connector 1680 with the first connection 1683 and the second connection 1687.

FIG. 17A illustrates a side view of a disposable wearable absorbent article 1700 with extensible sides 1720 as worn on a wearer according to embodiments of the present disclosure. The disposable wearable absorbent article 1700 includes a first area 1701, a back upper portion 1710, a region 1711, the extensible sides 1720, which are side ears, a back 1740, and a front 1760. The wearer includes small radius portions 1742, upper hips 1745, a belly 1750, and upper legs 1790. The extensible side 1720 can, in some embodiments, be the extensible side 820A of the embodiment of FIG. 8A and one or more of the elements of the embodiment of FIG. 17A can be the like-numbered element of the embodiment of FIG. 8A.

The disposable wearable absorbent article 1700 is configured to be worn by the wearer such that the region 1711 is disposed within the first area 1701 and within the extensible side 1720 so as to be proximate to the small radius portion 1742 of the wearer. The disposable wearable absorbent article 1700 is also configured to be worn by the wearer such that the first area 1701 is disposed above a posterior hip inflection protrusion 1762 of the wearer, as illustrated in FIG. 17B. The location of the upper hips 1745 is indicated by reference lines, which extend between FIGS. 17A and 17B.

FIG. 17B illustrates a side view of the wearer of FIG. 17A. The wearer includes the upper hips 1745, the belly 1750, the PHIP 1762, and the upper legs 1790.

Figure 18:
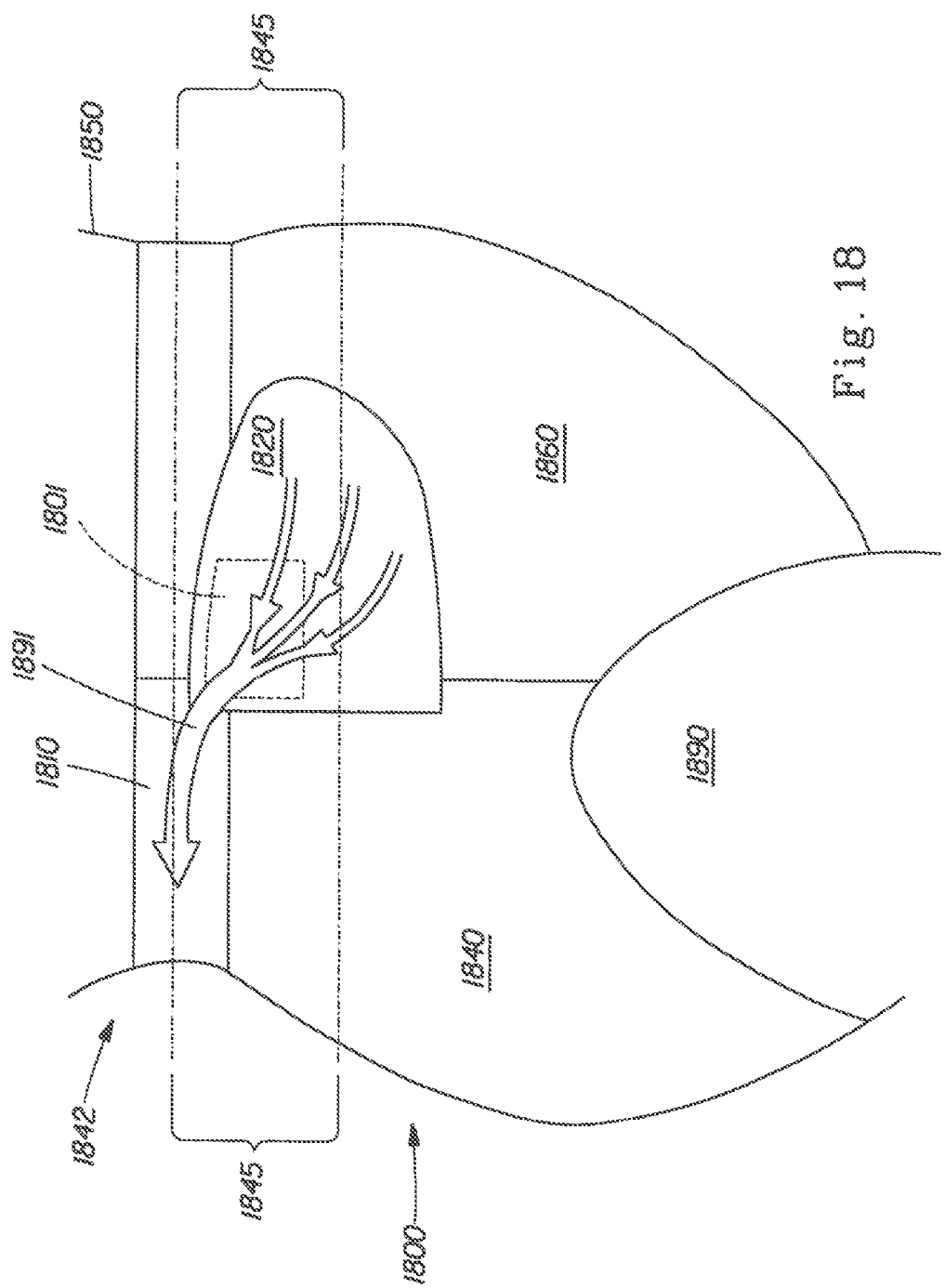
FIG. 18 illustrates a side view of a disposable wearable absorbent article, as worn by a wearer, with tensile forces directed through an upper portion of an extensible side of the disposable wearable absorbent article, according to embodiments of the present disclosure.

FIG. 18 illustrates a side view of a disposable wearable absorbent article 1820A, as worn by a wearer, with tensile forces 1891 directed through an upper portion of an extensible side 1820 of the disposable wearable absorbent article 1820A, according to embodiments of the present disclosure. The disposable wearable absorbent article 1820A includes a first area 1801, a back upper portion 1810, the extensible sides 1820, which are side ears, a back 1840, and a front 1860. The wearer includes small radius portions 1842, upper hips 1845, a belly 1850, and upper legs 1890. The extensible side 1820 can, in some embodiments, be the extensible side 820A of the embodiment of FIG. 8A and one or more of the elements of the embodiment of FIG. 18 can be the like-numbered element of the embodiment of FIG. 8A.

In the embodiment of FIG. 18, an upper portion of the extensible side 1820 of the disposable wearable absorbent article 1820A can be extended into greater tension, as described herein, so that the tensile forces 1891 can be directed from the disposable wearable absorbent article 1820A through the upper portion of the extensible side 1820 to the back upper portion 1810 of the disposable wearable absorbent article 1820A. As a result, the disposable wearable absorbent article 1820A can have extensible sides that extend with reasonably low forces and can fit snugly, stay in place, and not leak. Thus, the disposable wearable absorbent article 1820A can feel comfortable, look attractive, and perform well as the disposable wearable absorbent article 1820A is easy to apply and fits wearers well.

Embodiments of the present disclosure can be used with various features and structures for disposable wearable absorbent articles, as will be understood by one of ordinary skill in the art.

Other Method Details

All testing is to occur in conditions controlled to 22° C.±2° C., 50% Relative Humidity±10% Relative Humidity. Samples are conditioned at these conditions at least 2 hours, preferably 24 hours, prior to testing.

All distance measures made to the nearest 0.1 mm, using a calibrated caliper or image analysis system. All distance measures, other than article pitch, are to be made with the sample in a relaxed condition—that is having no external force applied to the sample to extend or compress it. Article pitch is to be measured with the article extended to a length that removes all elastically induced contraction.

All extensibility testing is to be performed using a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with diamond faced grips, wider than the width of the test specimen. The jaws are moved apart at a rate of 127 mm/min to the desired % elongation. If any slippage of the sample relative to the grips is noted, the grips or the sample should be modified. For example, grip pressure may be increased or an additional substrate (such as masking tape) may be bonded to the outside surface of the specimen outside the area to be tested yet in the area to be gripped to increase friction between the specimen and the grips.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable wearable absorbent article, comprising:
   a front, a back, and an elastically extensible side configured to connect the front and the back, wherein the elastically extensible side has a substantially laterally extensible area, which includes:
   a first area, bounded in part by at least a portion of a longitudinally outboard side edge;
   a second area, adjacent to and substantially laterally outboard from the first area, and bounded in part by at least a portion of the longitudinally outboard side edge;
   a third area, adjacent to and substantially longitudinally inboard to the first area, and bounded in part by at least a portion of the longitudinally inboard side edge;
   a fourth area, adjacent to and substantially laterally outboard from the third area, and bounded in part by at least a portion of the longitudinally inboard side edge; and
   wherein an overall lateral extensibility of the first area is substantially less than an overall lateral extensibility of the substantially laterally extensible area.

2. The article of claim 1, wherein the overall lateral extensibility of the first area is substantially less than:
   an overall lateral extensibility of the second area;
   an overall lateral extensibility of the third area; and
   an overall lateral extensibility of the fourth area.

3. The article of claim 2, wherein the overall lateral extensibility of the second area is substantially equal to:
   the overall lateral extensibility of the third area; and
   the overall lateral extensibility of the fourth area.

4. The article of claim 2, wherein the overall lateral extensibility of the second area is substantially less than:
   the overall lateral extensibility of the third area; and
   the overall lateral extensibility of the fourth area.

5. The article of claim 2, wherein:
   the overall lateral extensibility of the second area is substantially less than the overall lateral extensibility of the third area; and
   an overall lateral extensibility of the fourth area is substantially less than the overall lateral extensibility of the third area.

6. The article of claim 2, wherein the overall lateral extensibility of the fourth area is substantially less than:
   the overall lateral extensibility of the second area; and
   the overall lateral extensibility of the third area.

7. The article of claim 2, wherein the overall lateral extensibility of the third area is substantially less than the overall lateral extensibility of the second area.

8. The article of claim 2, wherein the overall lateral extensibility of the third area is substantially less than the overall lateral extensibility of the fourth area.

9. A disposable wearable absorbent article, comprising:
   a front, a back, and an elastically extensible side configured to connect the front and the back, wherein the elastically extensible side has a substantially laterally extensible area, which includes:
   a high modulus region with a particular overall lateral extensibility, bounded at least in part by a majority area; and
   the majority area, covering a majority of the substantially laterally extensible area, wherein the majority area has an overall lateral extensibility that is substantially greater than the particular overall lateral extensibility; and
   wherein the article is configured to be worn by a wearer such that the high modulus region is disposed within the extensible side proximate to a small radius portion of the wearer.

10. The article of claim 9, wherein a longitudinal dimension from a furthest longitudinally inboard point of the high modulus region to a back waist edge of the disposable wearable absorbent article is less than or equal to fifteen percent of a pitch of the disposable wearable absorbent article.

11. The article of claim 10, wherein the high modulus region is bounded in part by a laterally inboard side edge of the extensible side.

12. The article of claim 10, wherein the high modulus region is offset from a longitudinally outboard side edge of the extensible side.

13. The article of claim 10, wherein the high modulus region is bounded by a region boundary with an overall shape selected from the group, including:
   a half circle;
   a quarter circle;
   a half oval;

a quarter oval;
a tear-drop;
a radial pattern; and
a recognizable image.

14. The article of claim 10, wherein a widest lateral dimension of the high modulus region is configured to be disposed within the substantially laterally extensible area proximate to a longitudinally outboard side edge of the extensible side.

15. A disposable wearable absorbent article, comprising:
a front, a back, and an elastically extensible side configured to connect the front and the back, wherein the elastically extensible side has a substantially laterally extensible area, which includes:
  a high modulus region with a particular overall directional modulus of elasticity, wherein at least part of the high modulus region is disposed within a first area;
  the first area, disposed within a laterally inboard and longitudinally outboard portion of the substantially laterally extensible area, bounded in part by at least a portion of a longitudinally outboard side edge; and
  an outside area, outside the high modulus region, bounded in part by at least a portion of a longitudinally inboard side edge and at least a portion of the longitudinally outboard side edge, wherein substantially all of the outside area has a directional modulus of elasticity that is substantially less than the particular overall directional modulus of elasticity.

16. The article of claim 15, wherein:
substantially all of the high modulus region is mechanically activated with a first particular level of pre-strain; and
substantially all of the outside area is mechanically activated with a level of pre-strain that is greater than the first particular level of pre-strain.

17. The article of claim 15, wherein:
substantially all of the high modulus region is unactivated; and
substantially all of the outside area is mechanically activated.

18. The article of claim 15, wherein:
substantially all of the outside area includes one or more particular materials, which are bonded together to a particular lesser degree of bonding; and
substantially all of the high modulus region includes the particular materials, which are bonded together to a particular greater degree of bonding.

19. The article of claim 15, wherein:
substantially all of the outside area includes one or more particular materials; and
substantially all of the high modulus region includes the particular materials and a layer of an additional material, connected to the high modulus region.

20. The article of claim 15, wherein:
substantially all of the outside area includes one or more particular materials, which together have a particular lesser mass; and
substantially all of the high modulus region includes the particular materials, which together have a particular greater mass.

* * * * *